(12) United States Patent
Choi et al.

(10) Patent No.: US 11,021,586 B2
(45) Date of Patent: Jun. 1, 2021

(54) APPARATUS AND METHOD FOR MANUFACTURING CHANNEL-COUPLED SCAFFOLD

(71) Applicant: Korea Institute of Science and Technology, Seoul (KR)

(72) Inventors: Nakwon Choi, Seoul (KR); Sohyun Kim, Seoul (KR); Sohyeon Jeong, Seoul (KR); Eui Sung Yoon, Seoul (KR); Changjoon Justin Lee, Seoul (KR); Il-Joo Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 171 days.

(21) Appl. No.: 15/438,215

(22) Filed: Feb. 21, 2017

(65) Prior Publication Data

US 2017/0253860 A1      Sep. 7, 2017

(30) Foreign Application Priority Data

Mar. 3, 2016    (KR) ......................... 10-2016-0025885

(51) Int. Cl.
*B29C 43/18*      (2006.01)
*C08J 7/043*      (2020.01)
(Continued)

(52) U.S. Cl.
CPC .............. *C08J 7/043* (2020.01); *B29C 43/18* (2013.01); *C08J 7/0427* (2020.01); *C12M 21/08* (2013.01);
(Continued)

(58) Field of Classification Search
CPC ......... B29C 43/18; B29C 43/28; B29C 43/36; B29C 43/02; B29C 43/021; B29C 43/20;
(Continued)

(56) References Cited

U.S. PATENT DOCUMENTS

| | | |
|---|---|---|
| 6,544,762 B1 | 4/2003 | Tranquillo et al. |
| 7,981,345 B2 | 7/2011 | Yoo et al. |
| (Continued) | | |

FOREIGN PATENT DOCUMENTS

| | | |
|---|---|---|
| EP | 1 195 523 A2 | 4/2002 |
| JP | 5807542 B2 | 9/2015 |
| (Continued) | | |

OTHER PUBLICATIONS

Mazia et al., Adhesion of cells to surfaces coated with polylysine, Journal of Cell Biology, vol. 66, 1975, pp. 198-200.*
(Continued)

*Primary Examiner* — Allison M Fox
*Assistant Examiner* — Qing Xu
(74) *Attorney, Agent, or Firm* — NSIP Law

(57) ABSTRACT

The present disclosure relates to an apparatus and a method for manufacturing a channel-coupled scaffold. The present disclosure provides a method for manufacturing a channel-coupled scaffold, which includes: (1) a step of compressing a first elastic substrate which includes a groove on the surface of the substrate to close the groove; (2) a step of loading a scaffold composition onto the closed groove; and (3) a step of restoring the elastic substrate. The present disclosure also provides an apparatus for manufacturing a channel-coupled scaffold, which includes: a first elastic substrate which includes a groove on the surface of the substrate and onto which a scaffold composition is loaded: and a compression module which compresses the width of the groove of the elastic substrate to close it. The apparatus or method may accumulate a microchannel controlling local mass transfer, and align a collagen fiber in the scaffold at the same time.

7 Claims, 27 Drawing Sheets

(51) Int. Cl.
*C08J 7/04* (2020.01)
*C12M 3/00* (2006.01)
*C12M 1/12* (2006.01)
*C12N 5/00* (2006.01)
*C12N 5/09* (2010.01)

(52) U.S. Cl.
CPC ........... *C12M 25/14* (2013.01); *C12N 5/0068* (2013.01); *C12N 5/0693* (2013.01); *B29C 2043/185* (2013.01); *B29K 2995/0046* (2013.01); *C08J 2383/04* (2013.01); *C08J 2465/00* (2013.01); *C12N 2513/00* (2013.01); *C12N 2533/30* (2013.01); *C12N 2533/54* (2013.01)

(58) Field of Classification Search
CPC . B29C 43/203; B29C 43/54; B29C 2043/185; B29C 2043/022; B29C 43/00; C12M 25/14; C12M 21/08; B29K 2995/0046; C08J 7/0427; C08J 2383/04; C08J 2465/00; C12N 2533/54
See application file for complete search history.

(56) References Cited

U.S. PATENT DOCUMENTS

| | | | |
|---|---|---|---|
| 8,597,717 B2 * | 12/2013 | Fuller | A61L 27/24 427/2.24 |
| 8,691,262 B2 | 4/2014 | Harris | |
| 2014/0370511 A1 | 12/2014 | Katasho et al. | |
| 2015/0361386 A1 | 12/2015 | Liu et al. | |
| 2016/0109450 A1 | 4/2016 | Lee et al. | |
| 2016/0208210 A1 * | 7/2016 | Kim | C12M 23/12 |

FOREIGN PATENT DOCUMENTS

| | | |
|---|---|---|
| KR | 10-2011-0079623 A | 7/2011 |
| KR | 10-1250794 B1 | 4/2013 |
| KR | 10-2014-0135101 A | 11/2014 |
| KR | 10-2015-0014260 A | 2/2015 |
| KR | 10-2015-0088647 A | 8/2015 |
| WO | WO 2009/073548 A1 | 6/2009 |
| WO | WO 2010/022353 A1 | 2/2010 |
| WO | WO 2012/039994 A1 | 3/2012 |

OTHER PUBLICATIONS

Choi, Yoonseok, et al. "A Microengineered Pathophysiological Model of Early-Stage Breast Cancer." *Lab on a Chip* 15.16 (2015): 3350-3357. (8 pages, in English).

Gabriel, Nathan P., et al. "Cell-Laden Hydrogels in Integrated Microfluidic Devices for Long-Term Cell Culture and Tubulogenesis Assays." *Small* 9.18 (2013): 3076-3081. (7 pages, in English).

Hegde, Manjunath, et al. "Dynamic Interplay of Flow and Collagen Stabilizes Primary Hepatocytes Culture in a Microfluidic Platform." *Lab on a Chip* 14.12 (2014): 2033-2039. (7 pages, in English).

Puleo, Christopher M., et al. "Integration and Application of Vitrified Collagen in Multilayered Microfluidic Devices for Corneal Microtissue Culture." *Lab on a Chip* 9.22 (2009): 3221-3227. (7 pages, in English).

* cited by examiner

APPARATUS AND METHOD FOR MANUFACTURING CHANNEL-COUPLED SCAFFOLD

CROSS-REFERENCE TO RELATED APPLICATIONS

This application claims, under 35 U.S.C. § 119, the priority of Korean Patent Application No. 10-2016-0025885, filed on Mar. 3, 2016, in the Korean Intellectual Property Office, the disclosure of which is incorporated herein by reference in its entirety for all purposes.

TECHNICAL FIELD

The present disclosure relates to an apparatus and a method for manufacturing a channel-coupled scaffold.

DESCRIPTION OF GOVERNMENT-SUPPORTED RESEARCH AND DEVELOPMENT

This research was conducted by the Korea Institute of Science and Technology with support from the Brain Science Fundamental Technology Development Project of the Ministry of Science, ICT and Future Planning (sponsored by: National Research Foundation of Korea, project name: Embodiment of 3-dimensional in-vitro brain/glial cell network and development of platform for stimulation/measurement, project ID: 1711029935).

BACKGROUND

As the organs and tissues of the human body are generated during development from the embryonic state, cells and extracellular matrices surrounding the cells are aligned with characteristic morphologies. Due to this structural characteristic, the cells located in each organ and tissue interact specifically with other nearby cells or the extracellular matrix surrounding the cells. This interaction plays a significant role in the function of each organ. As representative examples, brain, heart, central and peripheral nerve fascicles and muscles show very characteristic structures and disruption of these structures leads to severe developmental disorders. Since the technical concept of tissue engineering of embedding and culturing cells in a hydrogel, inducing them to grow similarly to a specific tissue and then transplanting into an organism was first reported in 1993 in the journal Science, 3-dimensional culturing of animal cells is being developed continuously mainly in the US as a method of culturing cells in various synthetic or natural polymeric biomaterials. For such organs as the liver, cartilage, kidneys, etc., attempts to establish physiological models under an environment more similar to the in-vivo environment than the existing 2-dimensional cell culturing method have been successful to some extent. The 3-dimensional culturing technology has been introduced not only for the normal organ models but also to establish pathological models, for example, mimicking the cellular microenvironment in cancerous tissues, and the cell-cell interaction and cell-extracellular matrix interaction that have been overlooked in the existing 2-dimensional cell culturing are being studied consistently. Since the mid-2000s, its application has extended to 3-dimensional culturing of stem cells. Especially, the brain is a complicated, but highly characteristically structured organ. The cell bodies of specific neurons are selectively distributed in a specific layer in the brain and the axons and dendrites extending from the neurons are aligned regularly along a specific direction. This structural characteristic plays a significant role in the signal transduction of the brain nerve tissue/network. It is known that abnormal alignment and structuring of the cranial nerve network during the embryonic stage lead to various mental disorders including autism. Representative technologies currently used to study the alignment of neural networks are in-utero electroporation and organotypic slice culture. However, these methods are very invasive and labor-intense and it is impossible to monitor the long period of developmental stages. In addition, because they are optimized to study specific regions of the brain, it is difficult to study other regions in the brain. With the brain mapping project recently started in the US and Europe, efforts to embody the brain nerve/tissue network in a 3-dimensional ex-vivo environment are made very actively. Accordingly, development of a technology that allows for culturing of neurons glial cells that constitute the brain in an aligned biomaterial structure is important and its demand will increase consistently. A representative biomaterial used for cell culturing is collagen, which is a fibrous material making up the largest part of the human extracellular matrix. Currently known technologies for aligning collagen fibers include application of 1) electric field or 2) magnetic field from an external apparatus, 3) contraction of collagen using cells embedded in the collagen and 4) flowing of a collagen solution through a narrow tube to utilize the force generated by fluid flow (shear force). However, the application of electric or magnetic field from an external apparatus may lack reproducibility and practicability and the cells stimulated by the electric or magnetic field may exhibit altered physiological activity and significant toxicity. In addition, with the methods described above, it is difficult to construct different types of collagen into an integrated 3-dimensional structure with desired shape and size and to align the collagen fibers at the same time.

Even if a 3-dimensional structure containing aligned fibers is manufactured, it is another problem to provide a desired material inside the structure similarly to the in-vivo environment in order to observe the interaction with the material contained in the structure. In particular, the existing 3-dimensional structure containing channels is manufactured using a membrane structure. However, use of the membrane structure is problematic in that transport of material between upper and lower channels is not easy or cell culturing is impossible. In addition, it is even more difficult to manufacture a 3-dimensional structure containing aligned fibers and, at the same time, manufacture it to include communicable channels such that interaction between materials can be observed.

REFERENCES OF RELATED ART

Patent Documents

WO 2009073548 A1.
U.S. Pat. No. 6,544,762 B1.
U.S. Pat. No. 8,691,262 B2.
U.S. Pat. No. 8,597,717 B2.

Non-Patent Document

Christopher M. Puleo et al., Integration and application of vitrified collagen in multilayered microfluidic devices for corneal microtissue culture, *Lab Chip.* 2009 Nov. 21; 9(22): 3221-7.

SUMMARY

The present disclosure is directed to providing a method for manufacturing a channel-coupled scaffold or an apparatus for manufacturing the same.

In an aspect, the present disclosure provides a method for manufacturing a channel-coupled scaffold, which includes: (1) a step of compressing a first elastic substrate which includes a groove on the surface of the substrate and onto which a scaffold composition is loaded to close the groove; (2) a step of loading a scaffold composition onto the closed groove; and (3) a step of restoring the elastic substrate.

In another aspect, the present disclosure provides an apparatus for manufacturing a channel-coupled scaffold, which includes: a first elastic substrate which includes a groove on the surface of the substrate and onto which a scaffold composition is loaded; and a compression module which compresses the width of the groove of the elastic substrate to close it.

The apparatus or method according to an aspect of the present disclosure may accumulate a microchannel controlling local mass transfer and align a collagen fiber in the scaffold at the same time, In accordance with the apparatus or method according to an aspect of the present disclosure, a channel-coupled scaffold can be manufactured by a simple method, i.e., compressing an elastic substrate, loading a scaffold composition thereonto and then restoring the elastic substrate, and microfibrils or cells included in the scaffold can be aligned in a specific direction. Therefore, the present disclosure is also useful for culturing of aligned cells because the physiological activity of the cells can be maintained and cytotoxicity can be prevented. Accordingly, cell culture models used in various researches can be easily produced and provided in large scale. In addition, the present disclosure is very useful because it can be used to align neurons and glial cells of the brain which are very sensitive to environmental change.

BRIEF DESCRIPTION OF DRAWINGS

FIG. 10A is a 3-dimensional image constructed using the ZEN software from a confocal microscopic image at 20× magnification and FIG. 10B is an orthogonal view image at 20× magnification. FIG. 10C is an image obtained at 40× magnification, FIG. 10D is an image obtained from FIG. 10C by conducting color mapping and FIG. 10E shows a polar plot obtained from the color-mapped image.

DETAILED DESCRIPTION OF EMBODIMENTS

Figure 1:
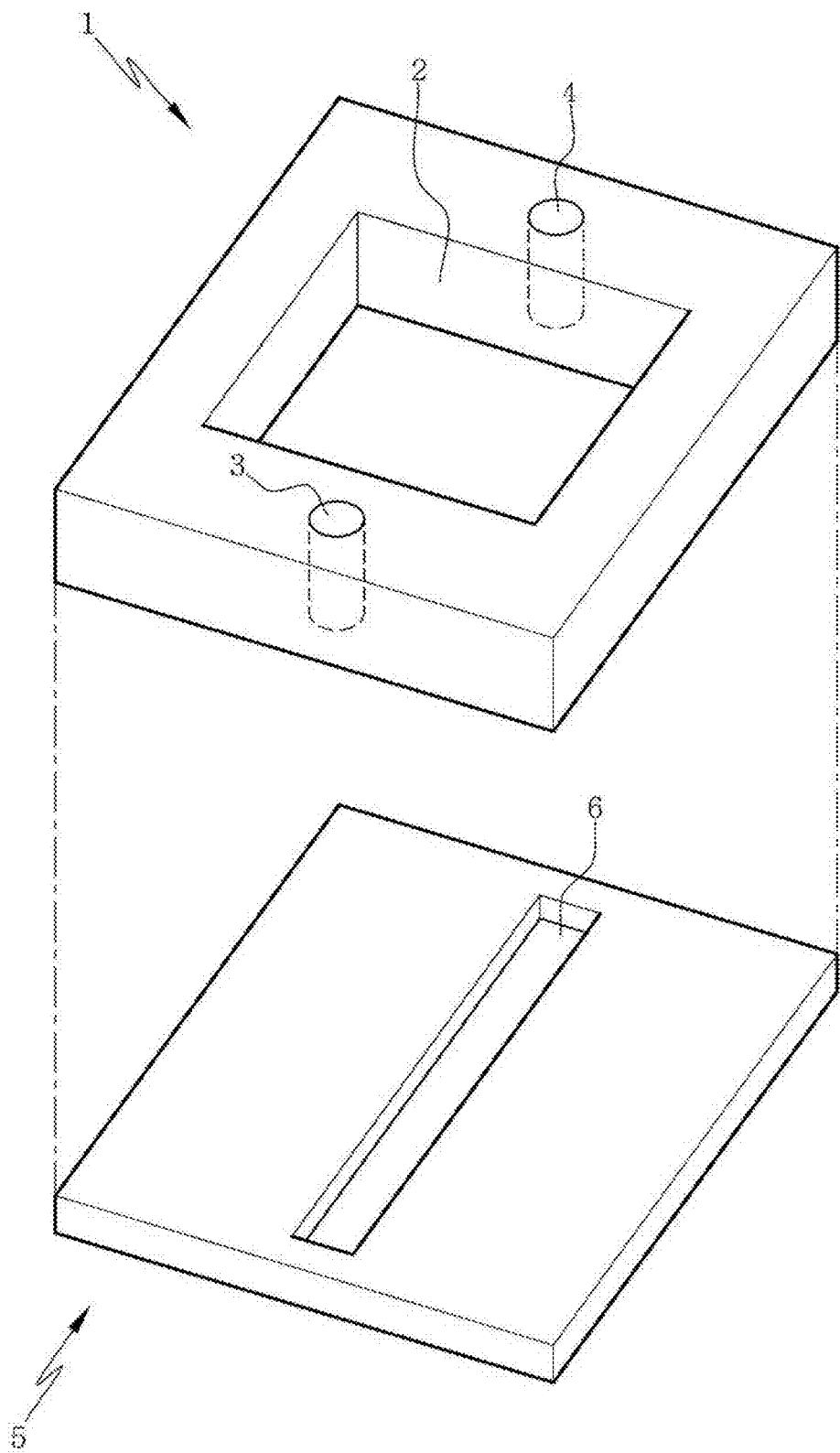
FIG. 1 is a perspective view of a first elastic substrate and a second elastic substrate constituting an apparatus for manufacturing a channel-coupled scaffold or a channel-coupled scaffold assembly according to an aspect of the present disclosure.

In an aspect, the present disclosure may relate to method for manufacturing a channel-coupled scaffold, which includes: (1) a step of compressing a first elastic substrate (or a channel layer elastic substrate) which includes a groove on the surface of the substrate to close the groove; (2) a step of loading a scaffold composition onto the closed groove; and (3) a step of restoring the elastic substrate.

In an aspect of the present disclosure, the term first elastic substrate may be used interchangeably with a channel layer elastic substrate and the term second elastic substrate may be used interchangeably with a well layer elastic substrate.

In an aspect of the present disclosure, the scaffold composition may be one or more of a microfibril, a cell or a mixture thereof.

In an aspect of the present disclosure, the microfibril may be one or more synthetic polymer fiber selected from a group consisting of nylon, polyacrylic acid, polycarbonate, polyurethane, poly(ethylene-vinyl acetate), polystyrene, polyvinyl alcohol, cellulose acetate and polyethylene oxide or one or more natural polymer fiber selected from a group consisting of elastin, gelatin, fibrinogen, fibrin, alginate, cellulose, silk fibroin, chitosan, laminin, actin and collagen. Specifically, in an aspect of the present disclosure, the microfibril is not limited as long as it is a fiber having directionality that can be used for cell culturing. In particular, the microfibril may be a collagen fiber.

In the present disclosure, the "substrate" is not limited as long as it is prepared from a material having elasticity. For example, the material having elasticity may be polydimethylsiloxane (PDMS). However, any material having elasticity widely known in the art may be used without limitation.

In the present disclosure, "elasticity" means the ability of an object to return to its original structure after its structure has been deformed by an external force, as obviously recognized by those of ordinary skill. Specifically, in the present disclosure, the "elastic substrate" may mean a substrate which, after it has been compressed by 5% or more, 10% or more, 15% or more, 20% or more, 30% or more, 35% or more, 40% or more, 45% or more, 50% or more, 55% or more, 60% or more, 70% or more or 80% or more of its width, can restore to 80% or more, 85% or more, 90% or more, 95% or more or 99% or more of its original width before the compression.

In the present disclosure, the "microfibril" refers to a fiber-like strand of sub-micrometer size, which is long, thin and bendable. The microfibril may be a synthetic or natural polymer fiber. For example, it may be a biofiber such as a collagen fiber or an actin fiber.

In an aspect of the present disclosure, the cell may be a cell that can be cultured in vitro and can be obtained from a living organism. Specifically, the cell may be a neuron, a glial cell, a muscle cell, a solid cancer cell, a mesenchymal stem cell or a fibroblast.

In the present disclosure, the cell is not particularly limited as long as it is a cell that can be cultured in vitro and can be obtained from a living organism. Any cell that can be used for alignment or arrangement of cells in the art can be used without limitation.

In an aspect of the present disclosure, the method may further include, before the step (1), (1)' a step of coating the elastic substrate with an adhesive.

In an aspect of the present disclosure, the adhesive may be one or more selected from a group consisting of glutaraldehyde, polyethyleneimine, poly-L-lysine, poly-D-lysine and polydopamine. However, any adhesive widely used in the art that can be used to fix a scaffold composition such as a collagen gel into the well of the elastic substrate or one that can be easily recognized by those of ordinary skill may be used without limitation.

In an aspect of the present disclosure, the method may further include, after the step (2) and before the step (3), (2)' a step of maintaining the compressed state of the elastic substrate onto which the scaffold composition is loaded.

In an aspect of the present disclosure, in the step (2)', the compressed state of the elastic substrate may be maintained for 1-10 minutes. Specifically, in the step (2)', the compressed state of the elastic substrate may be maintained for 1 minute or longer, 2 minutes or longer, 3 minutes or longer, 4 minutes or longer, 5 minutes or longer, 6 minutes or longer, 7 minutes or longer, 8 minutes or longer, 9 minutes or longer, 10 minutes or longer, 20 minutes or longer, 30 minutes or longer, 40 minutes or longer or 1 hour or longer, or 1 hour or shorter, 40 minutes or shorter, 30 minutes or shorter, 20 minutes or shorter, 10 minutes or shorter, 9 minutes or shorter, 8 minutes or shorter, 7 minutes or shorter, 6 minutes or shorter, 5 minutes or shorter, 4 minutes or shorter, 3 minutes or shorter, 2 minutes or shorter or 1 minute or shorter.

In an aspect of the present disclosure, in the step (2)', the scaffold composition may be cured partially by maintaining the compressed state of the elastic substrate.

In an aspect of the present disclosure, in the step (1), the elastic substrate may be compressed along a direction perpendicular to the groove.

In an aspect of the present disclosure, the microfibril, cell or a mixture thereof included in the scaffold composition may be aligned along a direction parallel to the compression or restoration direction.

In an aspect of the present disclosure, in the step (3), a channel may be formed below the loaded scaffold composition as the elastic substrate is restored.

In an aspect of the present disclosure, the method may further include, after the step (3), (3)' a step of gelling the scaffold composition. The step (3)' may be performed between the step (3) and a step (4). Specifically, in an aspect of the present disclosure, the step (3)' may be performed by keeping the restored elastic substrate in an incubator at 30-40° C., specifically 37° C., for 10 minutes to 1 hour, for 20-40 minutes or for 30 minutes.

In an aspect of the present disclosure, the method may further include, after the step (3), (4) a step of incubating the elastic substrate containing the aligned scaffold composition in a cell culture medium. Specifically, the incubation in the step (4) may be performed in an incubator. The incubation time may be 1-5 days, specifically 2-4 days or about 3 days and the incubation temperature may be 30-40° C., specifically 35-39° C., more specifically 36-38° C.

In an aspect of the present disclosure, as a second elastic substrate (well layer elastic substrate), a substrate including a well penetrating the second elastic substrate may be formed on the first elastic substrate (channel layer elastic substrate).

The elastic substrate used in an aspect of the present disclosure may be in the form of an assembly of the first elastic substrate (channel layer elastic substrate) and the second elastic substrate (well layer elastic substrate). In the present disclosure, the assembly of the first elastic substrate and the second elastic substrate may also be called an elastic substrate or an elastic substrate chip.

In an aspect of the present disclosure, the second elastic substrate may further include an inlet and an outlet connected to both ends of the channel of the first elastic substrate.

In an aspect of the present disclosure, in the step (2), the scaffold composition may be loaded into the well.

In an aspect of the present disclosure, the elastic substrate may be formed of an elastomer. In the present disclosure, the elastic substrate may be any substrate having elasticity as described above and may refer to the first elastic substrate, the second elastic substrate, the channel layer elastic substrate, the well layer elastic substrate, the assembly of the first elastic substrate and the second elastic substrate, the elastic substrate chip or a channel-coupled scaffold assembly.

In an aspect of the present disclosure, the elastomer may be one or more selected from a group consisting of natural polyisoprene, synthetic polyisoprene, polybutadiene, chloroprene rubber, butyl rubber, styrene-butadiene rubber, nitrile rubber, ethylene propylene rubber, ethylene propylene diene rubber, epichlorohydrin rubber, polyacrylic rubber, silicone rubber, fluorosilicone rubber, a fluoroelastomer, polyether block amide, chlorosulfonated polyethylene, ethylene-vinyl acetate and polydimethylsiloxane. Specifically, in an aspect of the present disclosure, the elastomer constituting the elastic substrate may be any material having elasticity which is widely known in the art or which can be easily selected by those skilled in the art. Examples include natural polyisoprene, synthetic polyisoprene, polybutadiene, chloroprene rubber (polychloroprene or neoprene), butyl rubber (copolymer of isobutylene and isoprene), halogenated butyl rubber (chlorobutyl rubber or bromobutyl rubber), styrene-butadiene rubber, nitrile rubber (copolymer of butadiene and acrylonitrile), hydrogenated nitrile rubber, ethylene propylene rubber (copolymer of ethylene and propylene), ethylene propylene diene rubber (terpolymer of ethylene, propylene and a diene component), epichlorohydrin rubber, polyacrylic rubber, silicone rubber, fluorosilicone rubber, a fluoroelastomer (Viton, Technoflon, etc.), a perfluoroelastomer, polyether block amide, chlorosulfonated polyethylene, ethylene-vinyl acetate, etc.

In an aspect of the present disclosure, in the step (1), the elastic substrate may be compressed by 5-80% of its original width before the compression along a direction perpendicular to the groove. Specifically, in an aspect of the present disclosure, the elastic substrate may be compressed by 5% or more, 10% or more, 15% or more, 20% or more, 25% or more, 27% or more, 29% or more, 30% or more, 32% or more, 34% or more, 36% or more, 38% or more, 40% or more, 42% or more, 44% or more, 46% or more, 48% or more, 50% or more, 52% or more, 54% or more, 56% or more, 58% or more, 60% or more, 65% or more, 70% or more or 80% or more or may be compressed by 80% or less, 70% or less, 65% or less, 60% or less, 58% or less, 56% or less, 54% or less, 52% or less, 50% or less, 48% or less, 46% or less, 44% or less, 42% or less, 40% or less, 38% or less, 36% or less, 34% or less, 32% or less, 30% or less, 28% or less, 26% or less, 24% or less, 22% or less, 20% or less, 15% or less, 10% or less or 5% or less of its original width before the compression along a direction perpendicular to the groove.

In an aspect of the present disclosure, in the step (1), the elastic substrate may be compressed to close 30-100% of the width of the groove. Specifically, in an aspect of the present disclosure, the elastic substrate may be compressed to close 10% or more, 20% or more, 30% or more, 40% or more, 50% or more, 60% or more, 70% or more, 75% or more, 80% or more, 85% or more, 90% or more, 95% or more, 99% or more or 100% or to close 100% or less, 99% or less, 95% or less, 90% or less, 85% or less, 80% or less, 75% or less, 70% or less, 60% or less, 50% or less, 40% or less, 30% or less, 20% or less or 10% or less of the width of the groove.

In an aspect of the present disclosure, the method may be a method for manufacturing a channel-coupled scaffold by using an apparatus or a scaffold assembly according to an aspect of the present disclosure.

In an aspect, the present disclosure may relate to a scaffold assembly including a first elastic substrate (or channel layer elastic substrate) which includes a groove on the surface of the substrate and onto which a scaffold composition is loaded, wherein the groove forms a channel when a scaffold composition is loaded thereonto.

In an aspect of the present disclosure, the scaffold assembly may include a second elastic substrate (or well layer elastic substrate) which is located on the first elastic substrate and includes a well penetrating the substrate, wherein the scaffold composition is loaded into the well.

In an aspect of the present disclosure, the assembly may further include a scaffold composition which is loaded onto the groove of the first elastic substrate.

In an aspect, the present disclosure may relate to an apparatus for manufacturing a channel-coupled scaffold, which includes: the scaffold assembly according to an aspect of the present disclosure; and a compression module which compresses the width of the groove of the first elastic substrate to close it.

In an aspect, the present disclosure may relate to an apparatus for manufacturing a channel-coupled scaffold, which includes: a first elastic substrate (or channel layer elastic substrate) which includes a channel on the surface of the substrate and onto which a scaffold composition is loaded; and a compression module which compresses the width of the channel of the elastic substrate to close it.

In an aspect of the present disclosure, the apparatus may further include a second elastic substrate (or well layer elastic substrate) which is located on the first elastic substrate and includes a well penetrating the substrate, wherein the scaffold composition is loaded into the well.

In an aspect of the present disclosure, the compression module may include: a compression plate which contacts with two parallel sides of the elastic substrate; a compressor which compresses the elastic substrate by operating the compression plate; and a controller which controls the movement of the compressor.

In an aspect of the present disclosure, the elastic substrate may further contain an adhesive coated on the surface thereof.

In an aspect of the present disclosure, the controller may compress the width of the elastic substrate by 5-80% along a direction perpendicular to the groove by operating the compressor. Specifically, the controller may compress the width of the elastic substrate along a direction perpendicular to the groove in the same manner as in the step (1) of the method according to an aspect of the present disclosure.

In an aspect of the present disclosure, the controller may close 30-100% of the width of the groove by operating the compressor. Specifically, the controller may close the width of the groove in the same manner as in the step (1) of the method.

In an aspect of the present disclosure, there may be two or more compression plates. Specifically, one of the compression plates may be fixed and the other may compress the elastic substrate as it is operated by the compressor. Also, the elastic substrate may be compressed as the compression plate contacting with the elastic substrate is operated.

In an aspect of the present disclosure, the compressor may include two or more male screws and female screws. In an aspect of the present disclosure, the female screws of the compressor may be connected to the compression plate.

In an aspect of the present disclosure, the controller may include a rubber belt which connects the female screws of the compressor with each other. Specifically, the compression plate may be moved by operating the female screws by the rubber belt of the controller and the elastic substrate contacting with the compression plate may be compressed through this movement.

In an aspect of the present disclosure, the compression module is not limited as long as it is one that can compress the width of the elastic substrate, which is widely known in the art or can be easily selected by those skilled in the art. For example, a hydraulic cylinder or a pneumatic cylinder may be used. In an aspect of the present disclosure, the compression plate is not limited as long as it can contact with the elastic substrate and compress it.

Specifically, in an aspect of the present disclosure, the first elastic substrate (or channel layer elastic substrate) and the second elastic substrate (well layer elastic substrate) may be configured as shown in FIG. 1. Referring to FIG. 1, the first elastic substrate 5 may include a channel 6 which is formed on the center surface of the substrate in the form of a groove. The shape and depth of the channel are not limited within the ranges that can be easily changed by those of ordinary skill. And, the second elastic substrate 1 may include a well 2 penetrating the substrate at the center of the substrate and may further include an inlet 3 and an outlet 4 which are connected to both ends of the channel of the first elastic substrate.

Figure 2:
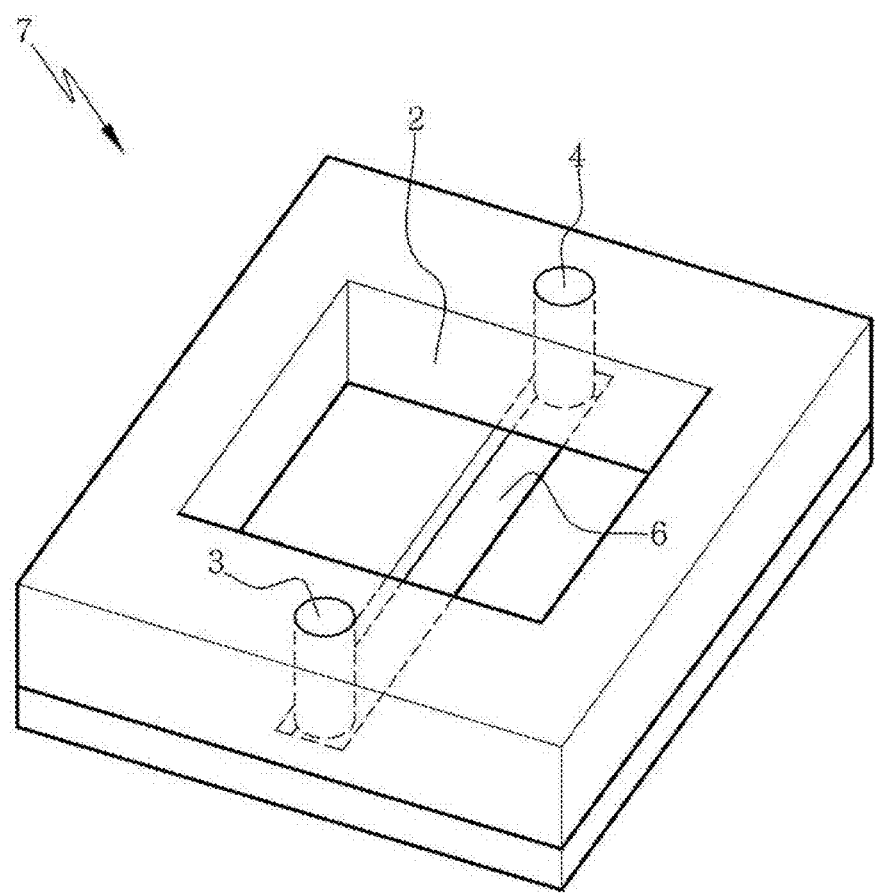
FIG. 2 is a perspective view of a PDMS chip or an elastic substrate chip wherein a first elastic substrate and a second elastic substrate constituting an apparatus or an assembly according to an aspect of the present disclosure are coupled with each other.

Referring to FIG. 2, the second elastic substrate may be assembled on the first elastic substrate to form an assembly 7. In the present disclosure, the assembly corresponds to a basic structural element of an elastic substrate chip or a channel-coupled scaffold assembly.

Figure 3A:
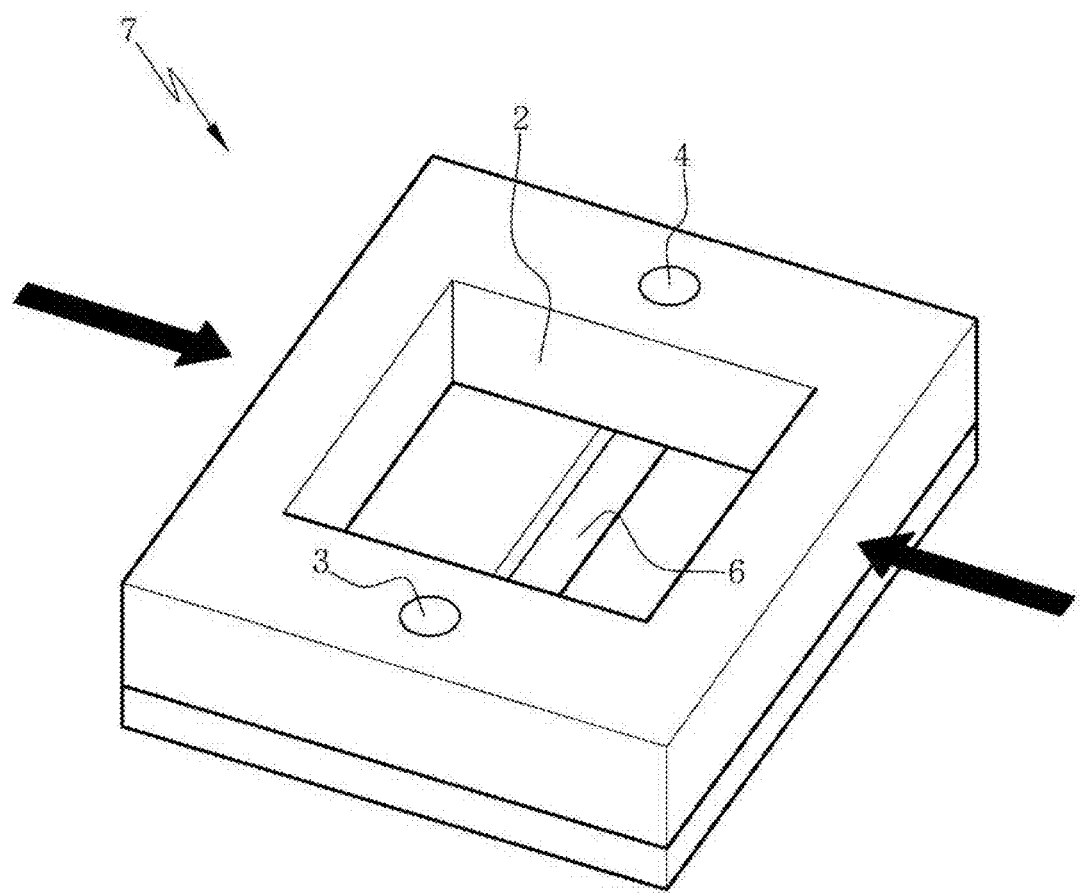
FIG. 3A is a perspective view showing a state before compressing an elastic substrate in a method or an apparatus according to an aspect of the present disclosure. The arrows indicate that the elastic substrate is compressed along a direction perpendicular to a groove.
Figure 3B:
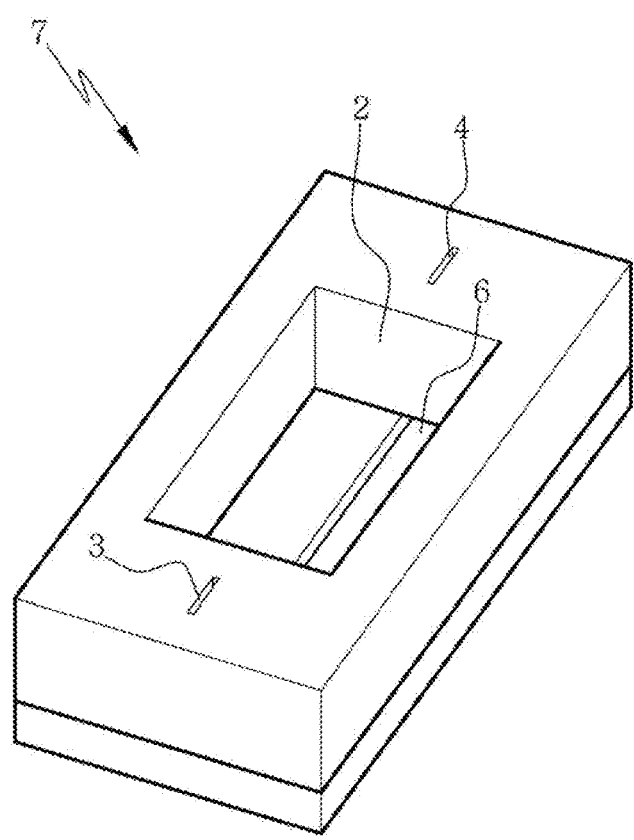
FIG. 3B is a perspective view showing a state where an elastic substrate is compressed in a method or an apparatus according to an aspect of the present disclosure.
Figure 3C:
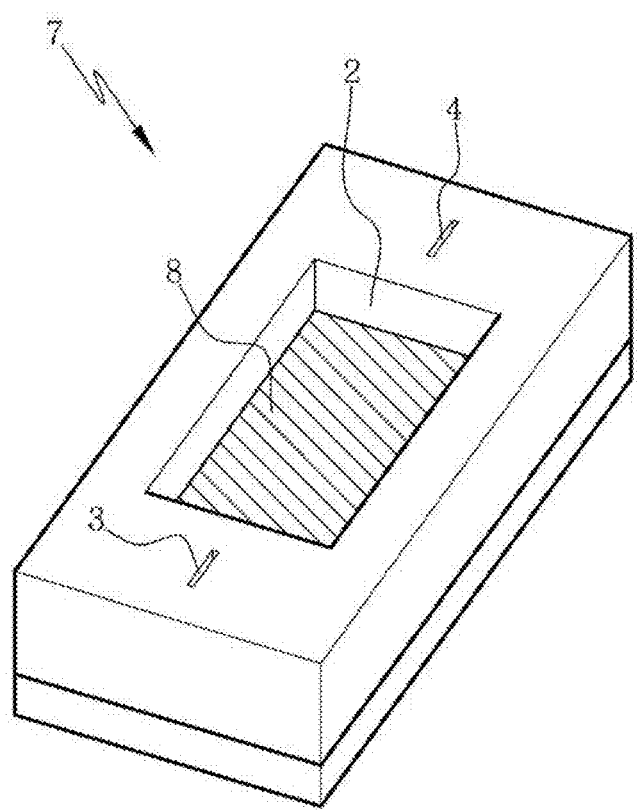
FIG. 3C is a perspective view showing a state where a scaffold composition is loaded onto a groove and into a well of a compressed elastic substrate in a method or an apparatus according to an aspect of the present disclosure.
Figure 3D:
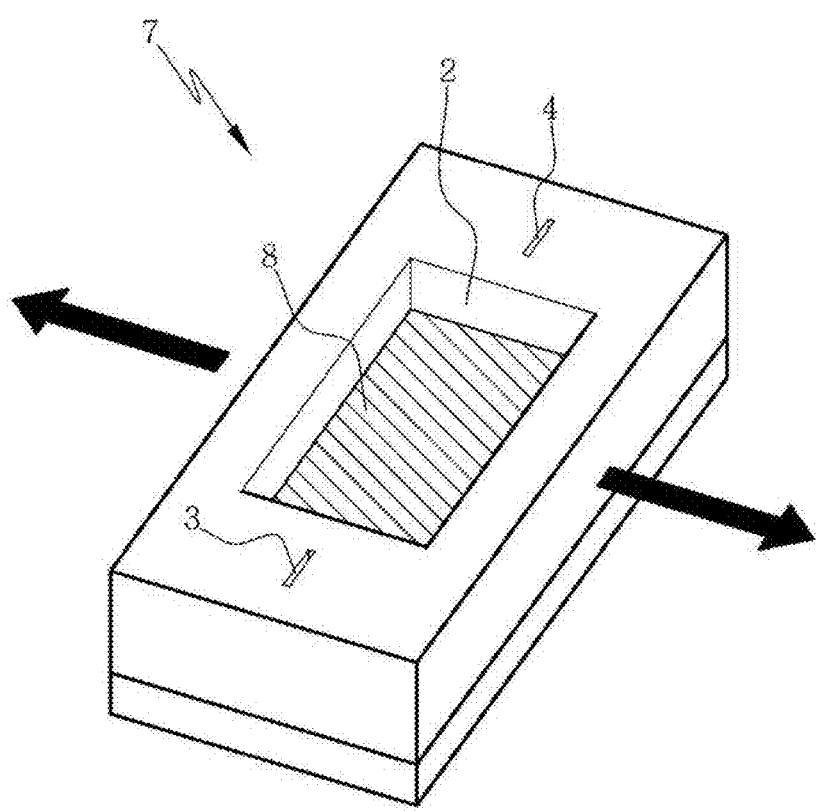
FIG. 3D is a perspective view showing a state where a compressed elastic substrate is restored in a method or an apparatus according to an aspect of the present disclosure. The arrows indicate that the elastic substrate is restored along a direction perpendicular to a groove.
Figure 3E:
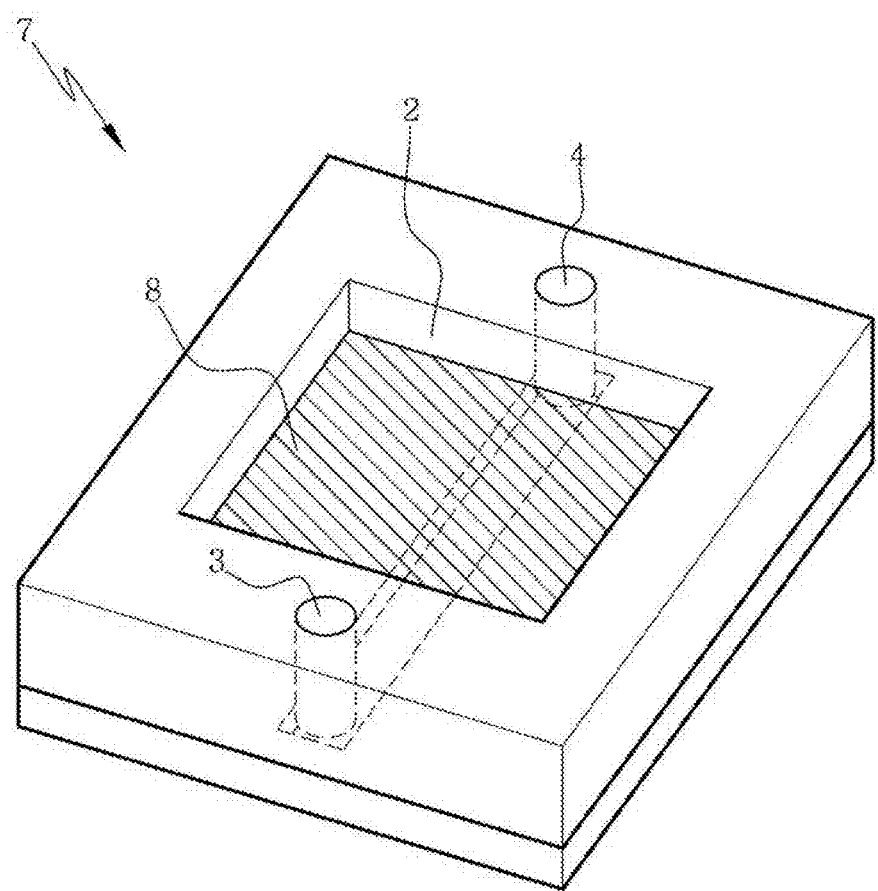
FIG. 3E is a perspective view showing a state where an elastic substrate has been restored in a method or an apparatus according to an aspect of the present disclosure.

FIG. 3A shows compression of the elastic substrate assembly 7 along a direction perpendicular to the channel 6. Through this compression, the channel 6 included in the first elastic substrate is closed as shown in FIG. 3B. Then, a scaffold composition 8 is loaded onto the channel 6 and into the well 2 as shown in FIG. 3C. After the scaffold composition is loaded, the compressed state is maintained for partial curing of the composition and then the elastic substrate assembly is restored to its original state as shown in FIG. 3D. As the elastic substrate assembly is restored to its original state, the microfibrils or cells contained in the scaffold composition are aligned along a compression direction or a direction parallel to the restoration direction, i.e., a direction perpendicular to the channel. With this, a channel-coupled scaffold or a scaffold assembly may be obtained as shown in FIG. 3E.

Figure 4:
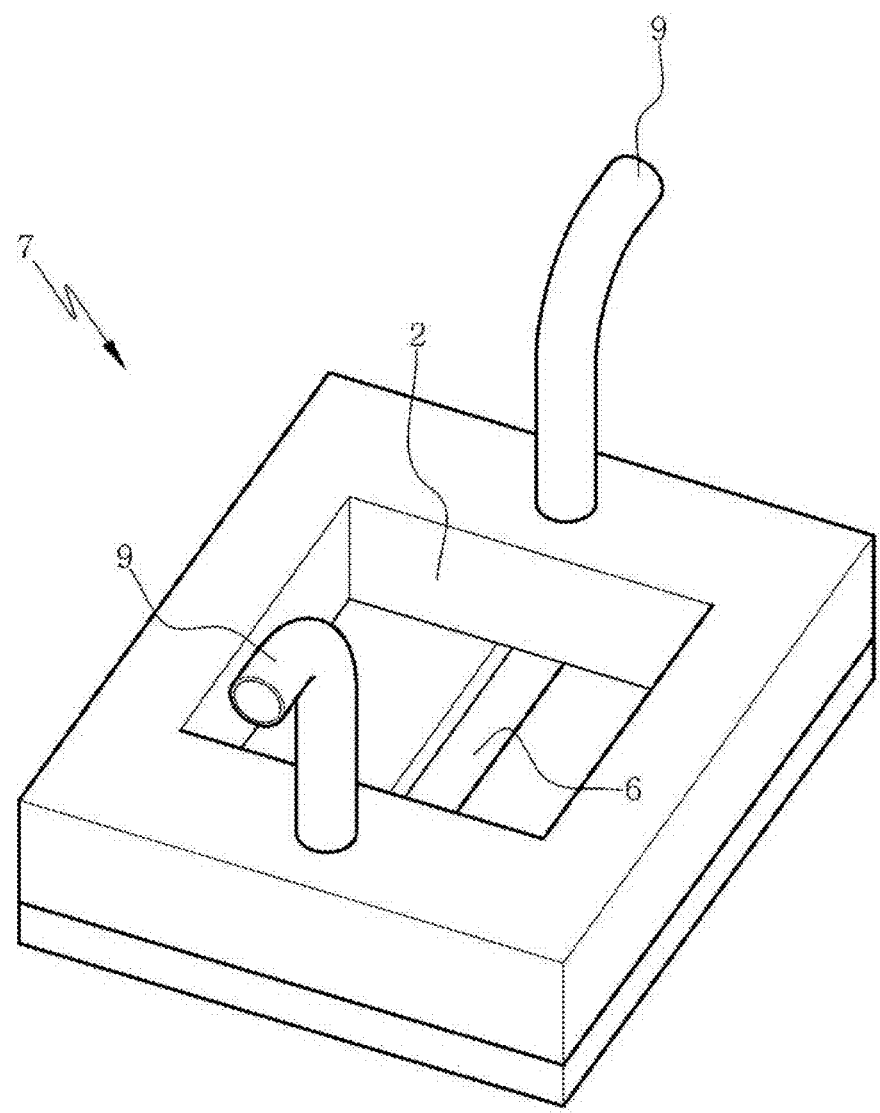
FIG. 4 is a perspective view showing a state where a tubing is connected to an inlet and an outlet of a second elastic substrate or a well layer substrate in an apparatus or an assembly according to an aspect of the present disclosure.

FIG. 4 shows a state where a tubing 9 is connected to the inlet and the outlet of the second elastic substrate in the method, the apparatus or the assembly according to an aspect of the present disclosure. Through the tubing 9, a material to be introduced into the channel of the channel-coupled scaffold may be injected.

Figure 5:
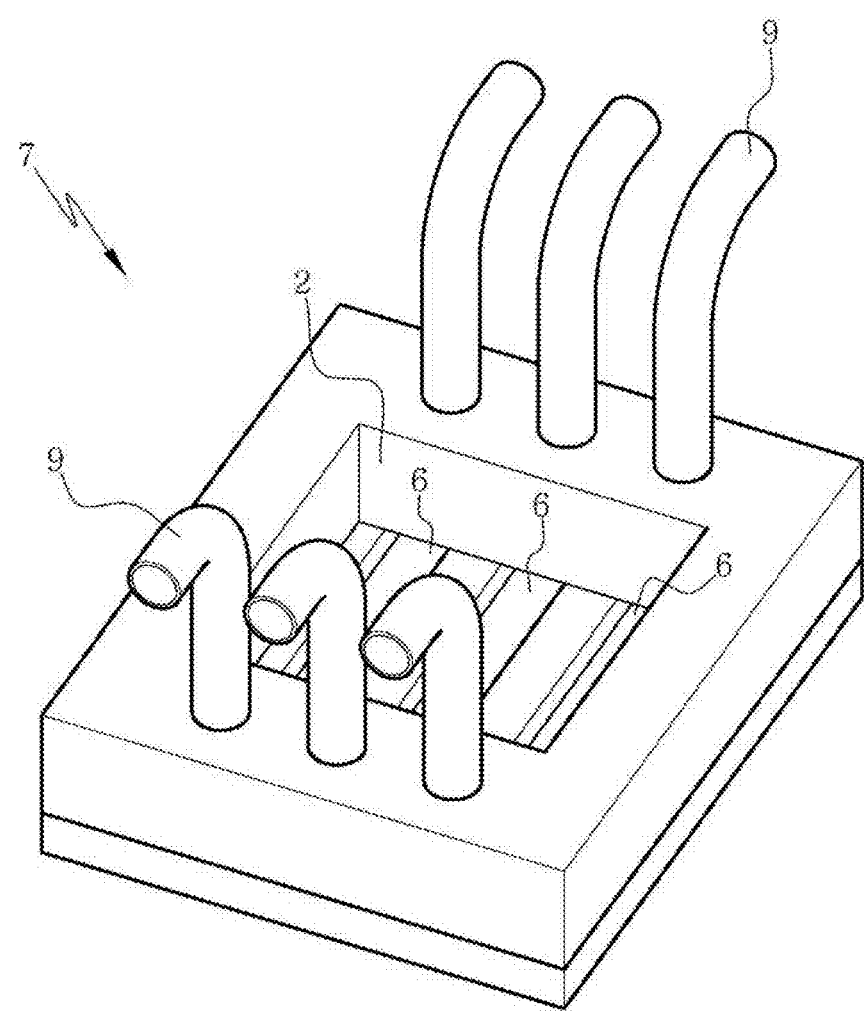
FIG. 5 is a perspective view showing a state where there are three inlets and three outlets and a tubing is connected to the inlets and the outlets in an apparatus or an assembly according to an aspect of the present disclosure.

FIG. 5 exemplarily shows a state where the first elastic substrate has two or more channels and the second elastic substrate has two or more sets of inlets and outlets in the method, the apparatus or the assembly according to an aspect of the present disclosure. When there are two or more channels, different materials may be introduced to the channels and it can be compared how the different materials are diffused in the scaffold.

Figure 6A:
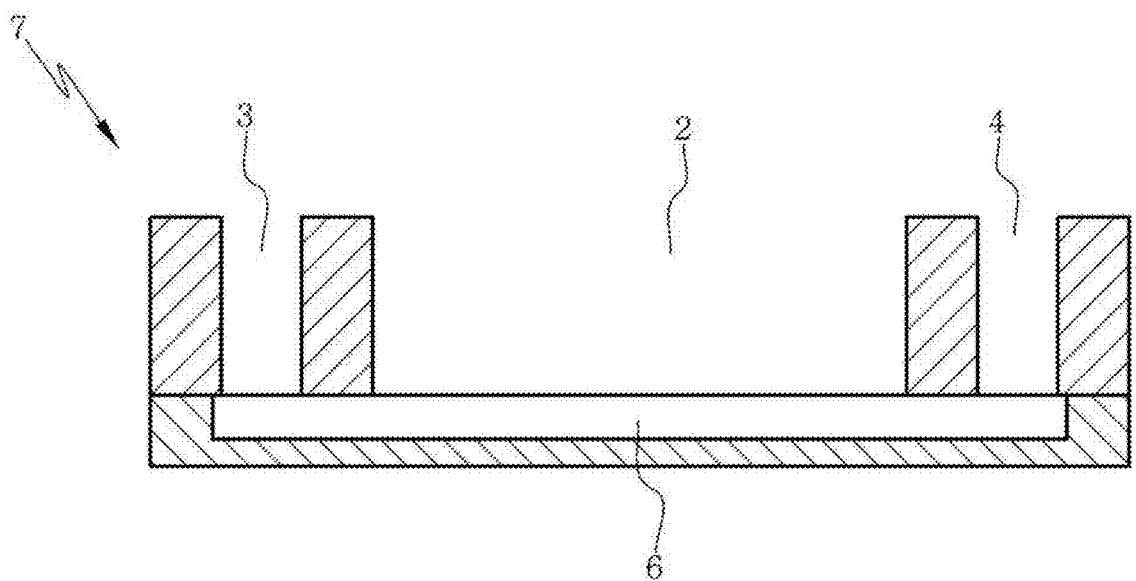
FIG. 6A is a cross-sectional view along an axis including a groove of an elastic substrate in an apparatus or an assembly according to an aspect of the present disclosure.

FIG. 6A shows the cross-section along an axis parallel to the channel direction of the elastic substrate chip or the elastic substrate assembly in the method, the apparatus or the assembly according to an aspect of the present disclosure. Referring to FIG. 6A, it can be seen that the inlet 3 and the outlet 4 included in the second elastic substrate are connected to both ends of the channel 6 included in the first elastic substrate and the well 2 of the second elastic substrate exists between the inlet and the outlet.

Figure 6B:
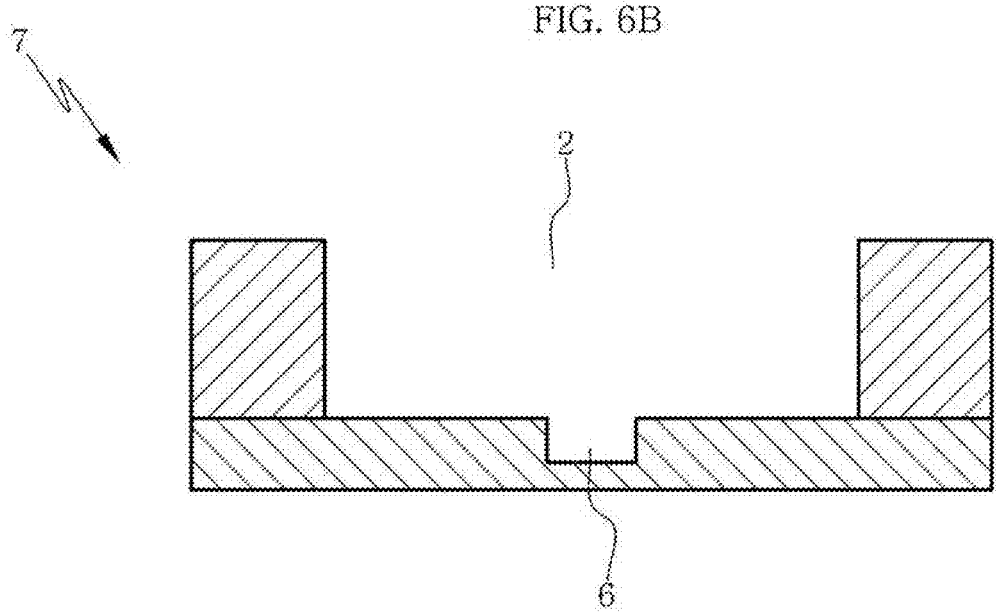
FIG. 6B is a cross-sectional view along an axis perpendicular to a groove of an elastic substrate in an apparatus or an assembly according to an aspect of the present disclosure.

FIG. 6B shows the cross-section along the axis perpendicular to the channel direction of the elastic substrate chip or the elastic substrate assembly in the method, the apparatus or the assembly according to an aspect of the present disclosure. Referring to FIG. 6B, it can be seen that the channel 6 exists on the first elastic substrate in the form of a groove and the well 2 of the second elastic substrate is formed thereon. Accordingly, in an aspect of the present disclosure, the scaffold composition is loaded into the well 2 on the channel 6 and exists there.

Figure 7A:
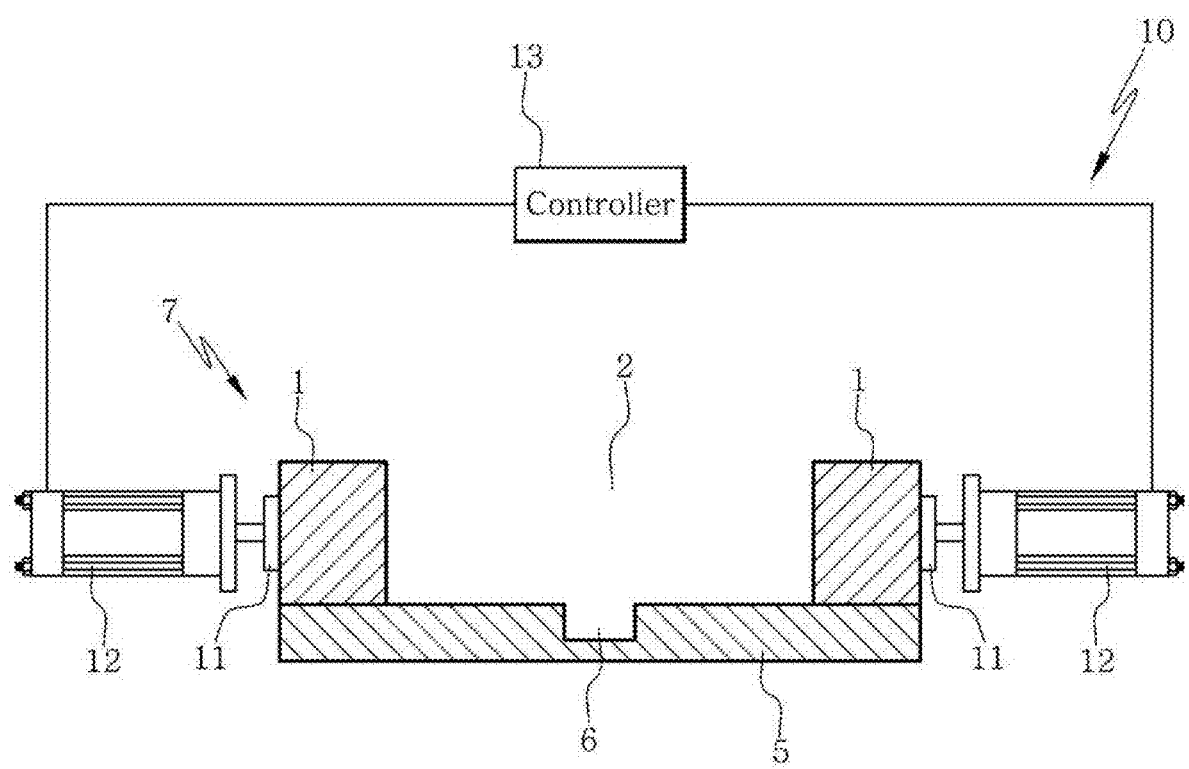
FIG. 7A shows an apparatus for manufacturing a channel-coupled scaffold according to an aspect of the present disclosure.

Specifically, the apparatus according to an aspect of the present disclosure may be configured as shown in FIG. 7A. Referring to FIG. 7A, the assembly 7 includes the first elastic substrate 5 including the channel 6 onto which the scaffold composition is loaded and the second elastic substrate 1 including the well 2. A compression module 10 which compresses the assembly may include a compression plate 11 which contacts directly with the elastic substrate and performs compression, a compressor 12 which compresses the elastic substrate by operating the compression plate and a controller 13 which is connected to the compressor and controls the movement of the compressor.

Figure 7B:
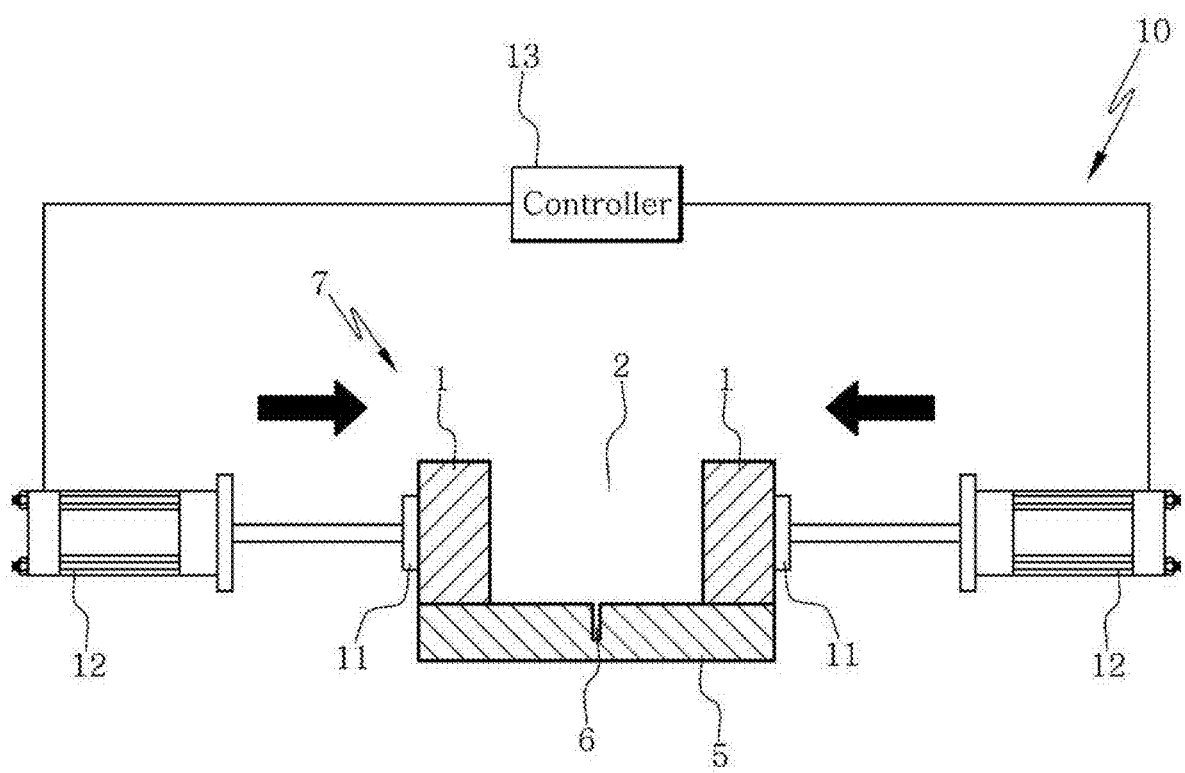
FIG. 7B shows compression of an elastic substrate in an apparatus or a method according to an aspect of the present disclosure.

FIG. 7B exemplary shows compression in the apparatus or the method according to an aspect of the present disclosure. The controller 13 controls the compressor 12 so as to compress the elastic substrate assembly 7 by operating the compression plate 11. The compressed width and the moving distance of the compression plate with time are controlled by the controller. Once the compression has been achieved as desired (e.g., 20-60% of the width before the compression), the compression is not performed any more.

Figure 7C:
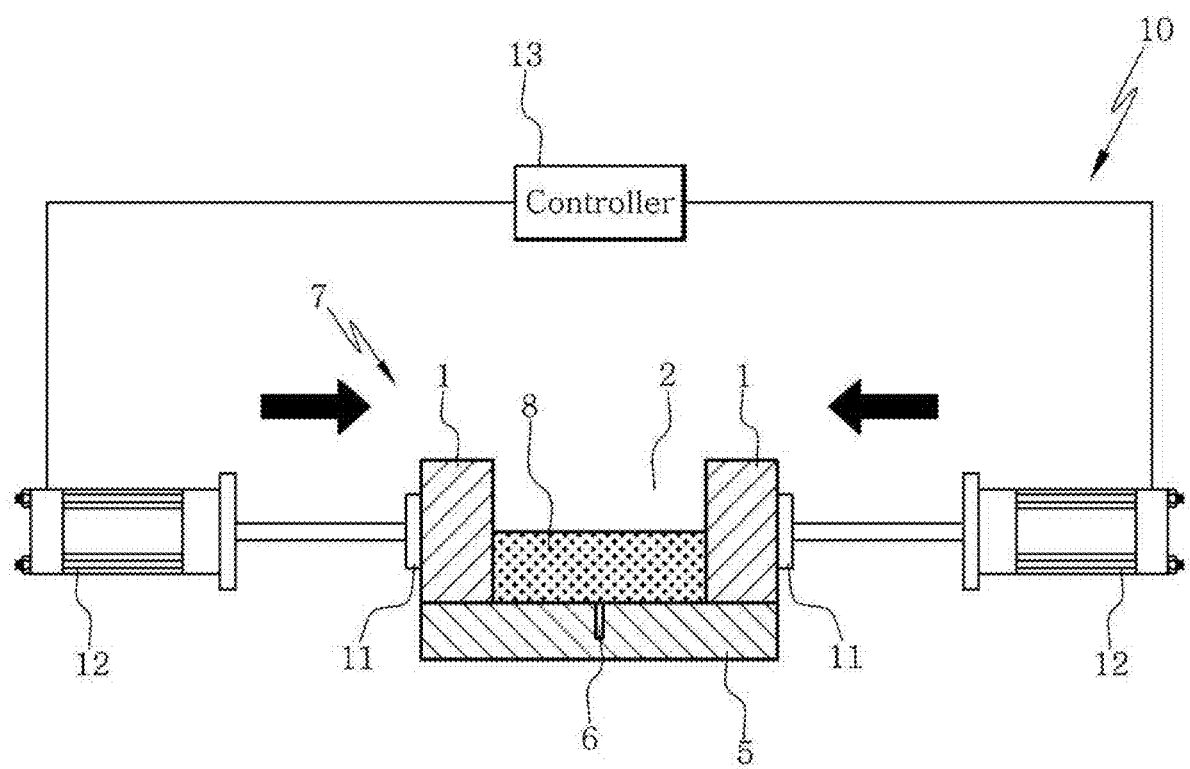
FIG. 7C shows a state where an elastic substrate has been compressed and a scaffold composition is loaded onto a groove and into a well in an apparatus or a method according to an aspect of the present disclosure.

FIG. 7C shows loading of the scaffold composition 8 onto the compressed elastic substrate assembly 7 in the apparatus or the method according to an aspect of the present disclosure. The scaffold composition 8 is loaded into the well 2 of the second elastic substrate 1 on the closed channel 6 of the first elastic substrate 5 and the compressed state is maintained so that the loaded scaffold composition can be cured partially.

Figure 7D:
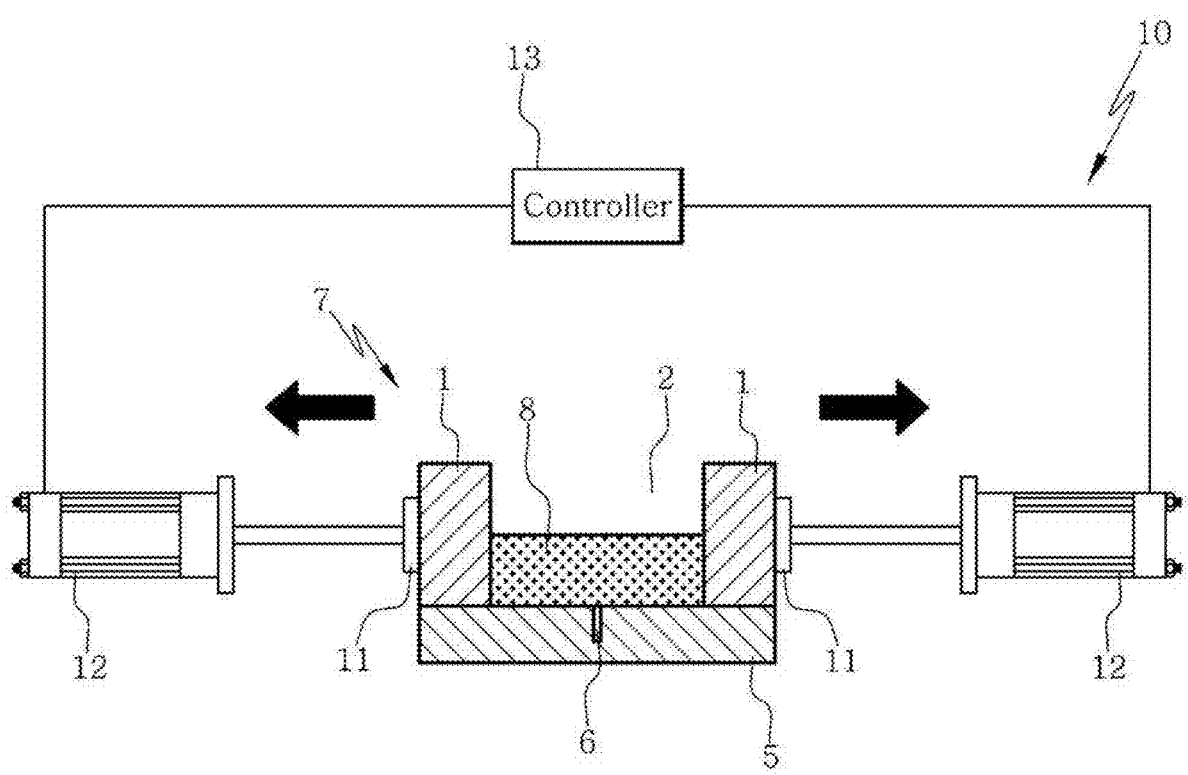
FIG. 7D shows restoration of an elastic substrate in an apparatus or a method according to an aspect of the present disclosure.
Figure 7E:
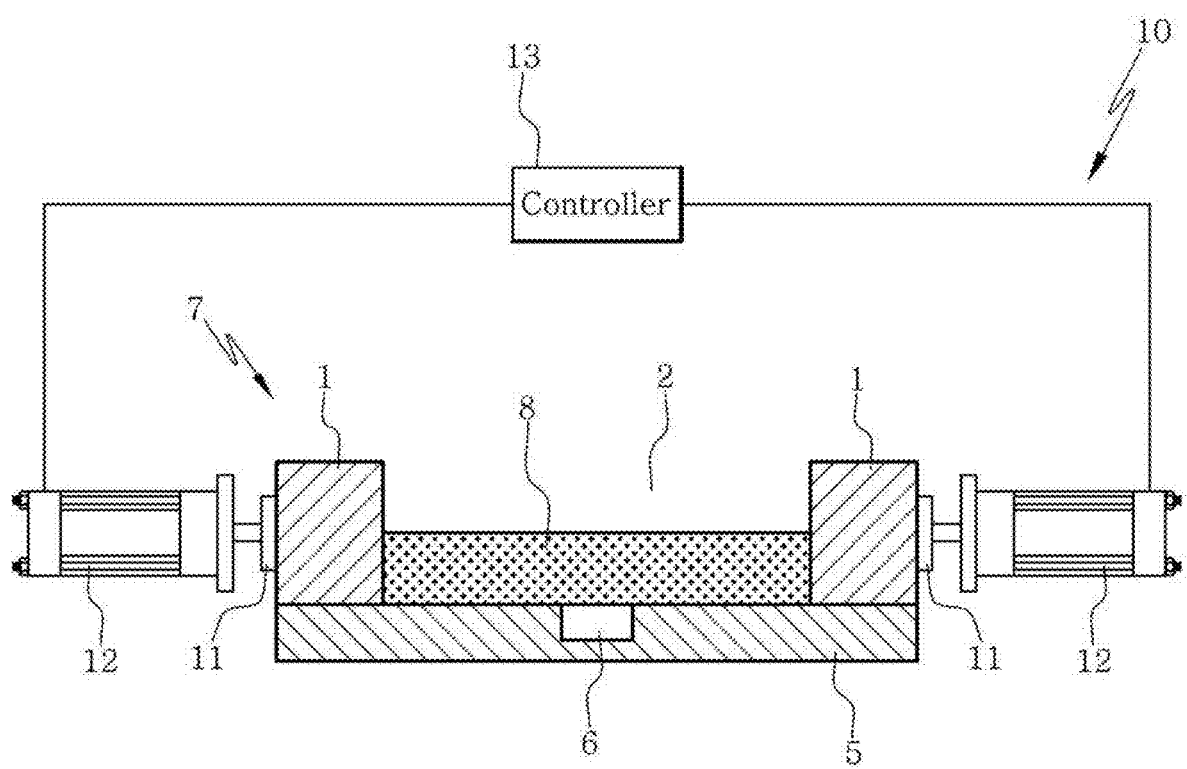
FIG. 7E shows a state where an elastic substrate has been restored in an apparatus or a method according to an aspect of the present disclosure.

FIG. 7D and FIG. 7E show restoration of the elastic substrate after the compression in the apparatus or the method according to an aspect of the present disclosure. The controller 13 restores the compression plate 11 in order to release the compressed state. As the elastic substrate assembly 7 having the scaffold composition 8 loaded is restored due to its inherent elasticity, a force is applied along a direction parallel to the restoration direction as shown in FIG. 7E. During this restoration, the microfibrils and cells contained in the scaffold composition 8 are aligned along the direction parallel to the restoration direction because the force is applied to the loaded scaffold composition 8 along the direction parallel to the restoration direction. In addition, the closed channel 6 is opened again during this restoration and, as a result, a scaffold having the channel 6 formed at the bottom portion can be prepared.

Figure 8:
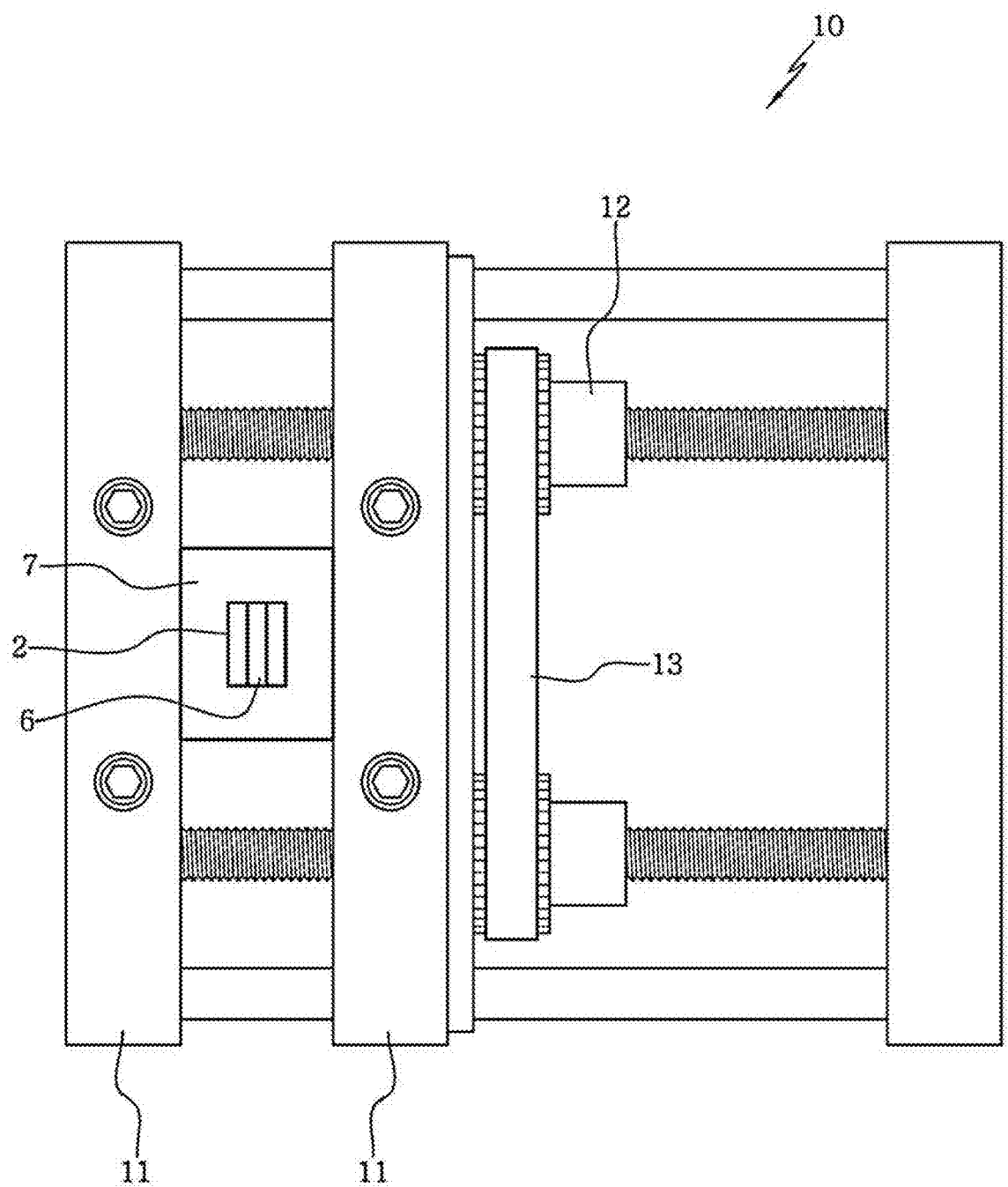
FIG. 8 shows an apparatus for manufacturing a channel-coupled scaffold according to an aspect of the present disclosure.

FIG. 8 shows an apparatus according to another aspect of the present disclosure. Referring to FIG. 8, an assembly of a first elastic substrate and a second elastic substrate, i.e., an elastic substrate chip, includes a groove 6 on the surface of the first elastic substrate and a well 2 which is included in the second elastic substrate and into which a scaffold composition is loaded. A compression module 10 which compresses the elastic substrate chip may include a compression plate 11 which directly contacts with the elastic substrate and performs compression, a compressor 12 which operates the compression plate to perform the compression and a controller 13 which is connected to the compressor and controls the compression. Specifically, of the two compressions plate 11, the compression plate not connected to the compressor 12 is fixed and the compression plate connected to the compressor 12 is moved by the compressor so as to compress the elastic substrate chip 7. The compressor 12 may include two or more female screws and male screws and the controller 13 may be a rubber belt engaged with the female screws of the compressor 12.

Hereinafter, the present disclosure will be described in more detail through examples. However, the following examples are for illustrative purposes only and it will be apparent to those of ordinary skill in the art that the scope of the present disclosure is not limited by the examples.

[Test Example 1] Confirmation of Structure of Channel-Coupled Scaffold Using Fluorescence-Labeled Collagen (TRITC-Labeled Collagen)

(1) Preparation of PDMS chip—1) Preparation of PDMS channel layer substrate: The size of a PDMS channel layer substrate was 20 mm (breadth)×20 mm (length)×3 mm (thickness) and the size of a channel located at the center of the substrate was 0.2 mm (width)×0.15 mm (depth)×15 mm (length). 2) Preparation of PDMS well layer substrate: The size of a PDMS well layer substrate was 20 mm (breadth)× 20 mm (length)×7 mm (thickness) and the size of a well located at the center was 5 mm (breadth)×5 mm (length)×7 mm (depth). 3) After treating with oxygen plasma (80 W, 20 sccm, 40 seconds), a PDMS chip was prepared by assembling the PDMS channel layer substrate with the PDMS well layer substrate as shown in FIG. 2.

(2) Then, the surface of the assembled chip was coated with polydopamine. Specifically, after adding 2 mg/mL dopamine hydrochloride in 10 mM Tris-HCl buffer (pH 8.5) into the PDMS well and conducting reaction at room temperature for 2 hours, the reaction solution was removed. After washing 3 times with distilled water, the chip was dried in a clean bench.

(3) The dried PDMS chip was compressed along a direction perpendicular to the channel of the PDMS chip using a compressor as shown in FIG. 8. The compression was performed so that the width of the well along the direction perpendicular to the channel was decreased from its original length of 5 mm to 2.5 mm.

(4) After loading 10 µL of a fluorescent material (tetramethylrhodamine, TRITC)-labeled collagen solution (2.5 mg/mL) into the well in the compressed state, the collagen solution was cured partially by maintaining the compressed state at room temperature for 4 minutes.

The fluorescent material-labeled collagen solution was prepared as follows. First, freeze-dried collagen was prepared by freeze-drying a high-concentration (8-11 mg/mL) collagen solution (Cat. 354249) derived from rat tail (Corning, USA). Then, after adding the freeze-dried collagen to 0.1 M sodium bicarbonate buffer (pH 9.0) to a concentration of 20 mg/mL, the solution was shaken at 4° C. for 24 hours so that the collagen was dissolved uniformly. After adding 10 mg/mL TRITC (tetramethylrhodamine) in DMSO (dimethyl sulfoxide) to the solution, the mixture was shaken at 4° C. in the dark for 24 hours. The molar ratio of collagen protein and the fluorescent material in the TRITC solution was set to 3:1. After the reaction, the collagen/TRITC solution was added to a dialysis tubing with a molecular weight cut-off of 25,000 Da and TRITC molecules remaining unbound to the collagen were removed by conducting dialysis in 0.1% acetic acid. The dialysis was conducted at 4° C. in the dark for at least 72 hours.

After the dialysis, the solution remaining in the tubing was recovered and freeze-dried in a freeze dryer (Ilshin Biobase, Kyunggi-do, Korea) at 40 mTorr and −60° C. for 3 days. A fluorescent material (TRITC)-labeled collagen solution was prepared by dissolving the freeze-dried collagen in 0.15% acetic acid to a concentration of 10 mg/mL.

(5) Then, the PDMS chip was restored from the compressed state. The restored chip was kept in an incubator at 37° C. for 30 minutes for complete gelling of the collagen solution.

(6) For cross-sectional imaging of the PDMS chip, the PDMS chip was immersed in a 0.25% glutaraldehyde solution for 1 hour so that the collagen protein was fixed. After taking out the chip, the chip was cut at the center portion using a razor along a direction perpendicular to the channel. Then, the cross-sectional images of the chip were obtained using the LSM700 confocal laser scanning microscope (Carl Zeiss, Germany). The result is shown in FIG. 9.

Figure 9:
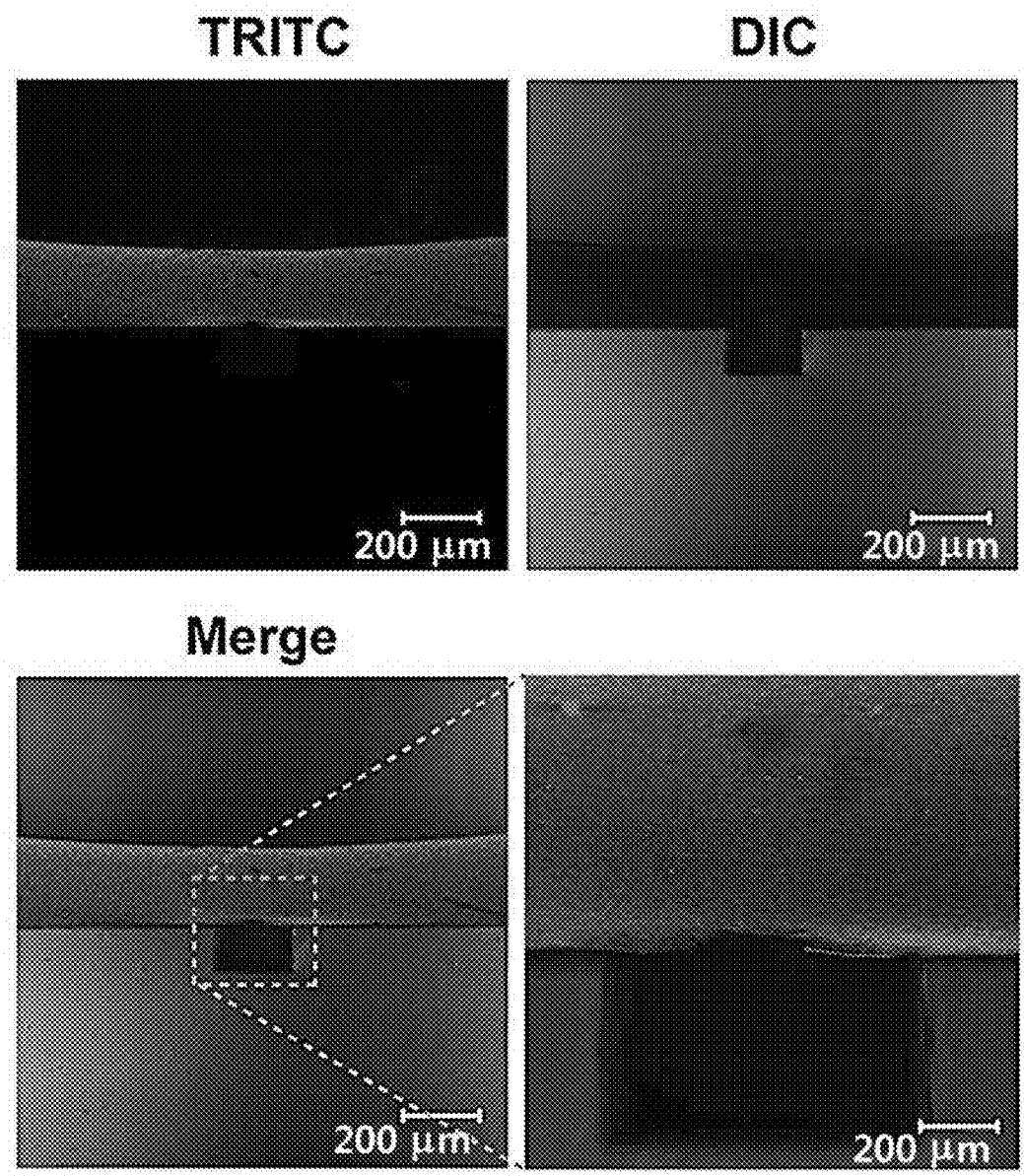
FIG. 9 shows the structure of a channel-coupled scaffold manufactured by an apparatus or a method according to an aspect of the present disclosure.

The structure of the TRITC-labeled collagen scaffold formed in the PDMS well can be confirmed from the TRITC image of FIG. 9. From the DIC image and the DIC-TRITC merged image, it can be seen that a channel-coupled collagen scaffold was formed as the TRITC-labeled collagen was formed on the channel without being introduced to the lower PDMS channel.

[Test Example 2] Confirmation of Alignment of Collagen Solution During Manufacturing of Channel-Coupled Scaffold Collagen gel was formed in the same manner as in (1) through (5) of Test Example 1. Then, a channel-coupled scaffold was prepared using a collagen solution not labeled with a fluorescent material.

The collagen solution not labeled with a fluorescent material was prepared by adding 10×DMEM (Sigma Aldrich, USA), DMEM (Lonza, Switzerland) and 0.5 N NaOH to a high-concentration (8-11 mg/mL) collagen solution (Cat. 354249) derived from rat tail (Corning, USA). The final concentration was 2.5 mg/mL and the acidity was about pH 7.

(1) For staining of the collagen gel obtained from the gelling in the incubator, the PDMS chip was immersed in 50 µM 5(6)-carboxytetramethylrhodamine succinimidyl ester (5(6)-TAMRA-SE; Invitrogen, USA) in PBS (phosphate-buffered saline; Lonza, USA). After reaction at room temperature for 1 hour, the chip was taken out of the solution and washed 3 times with PBS.

(2) The stained collagen gel was imaged using the LSM700 confocal laser scanning microscope (Carl Zeiss, Germany). Z-stacked images were obtained at 20× magnification and the image of the collagen fibers was obtained at 40× magnification. The result is shown in FIG. 10A to FIG. 10E.

(3) Specifically, a 3-dimensional image (FIG. 10A) and an orthogonal view image (FIG. 10B) were obtained from the confocal microscopic images obtained at 20× magnification using the ZEN software.

Figure 10A:
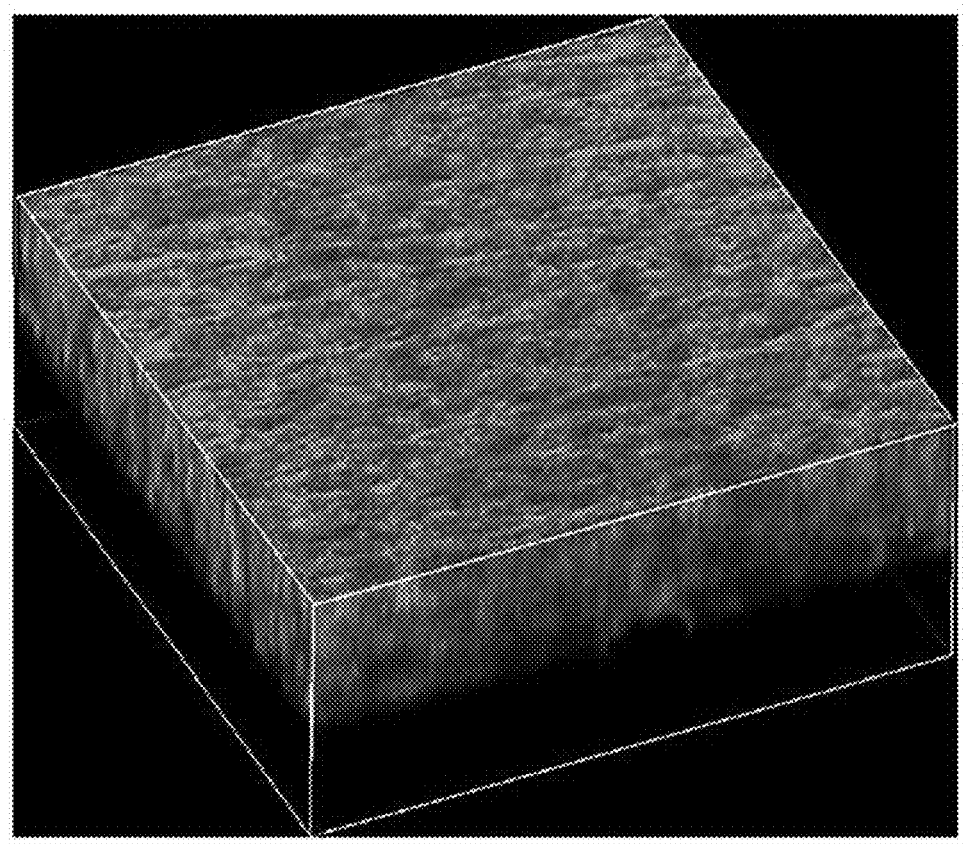
FIG. 10A to FIG. 10E show alignment of collagen fibers included in a scaffold and their alignment direction in manufacturing a channel-coupled scaffold by an apparatus or a method according to an aspect of the present disclosure.
Figure 10B:
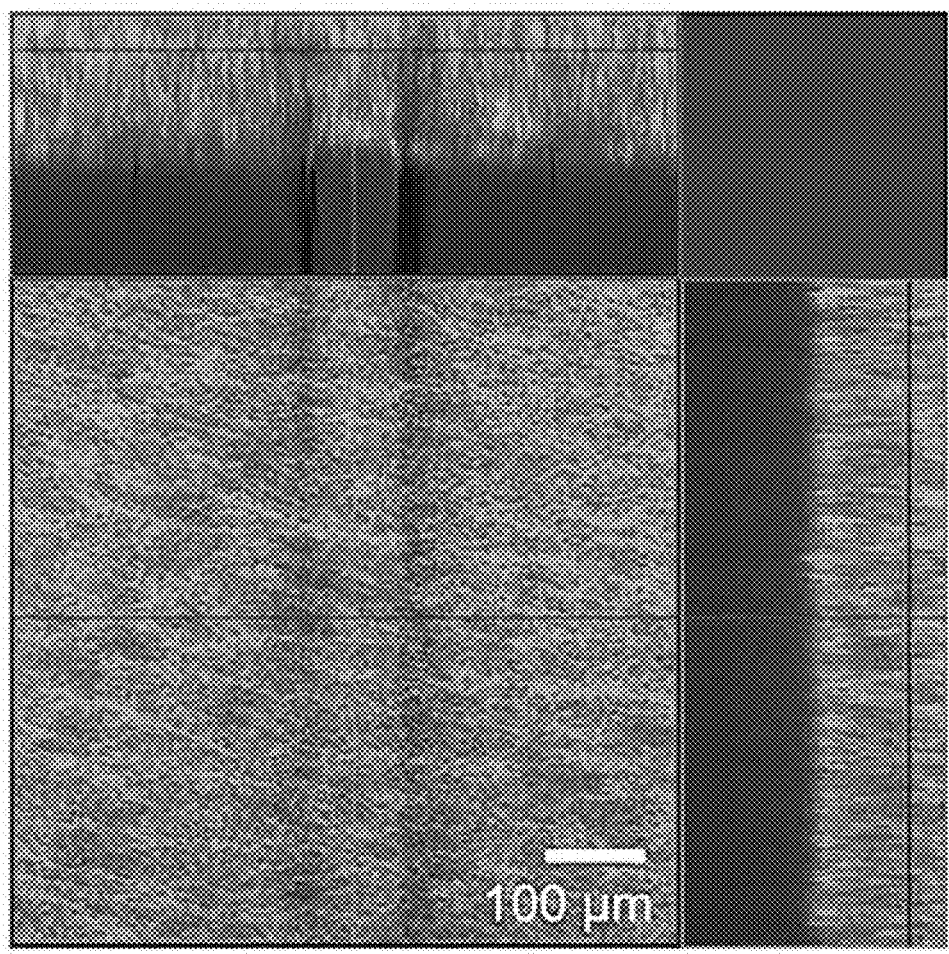
Figure 10C:
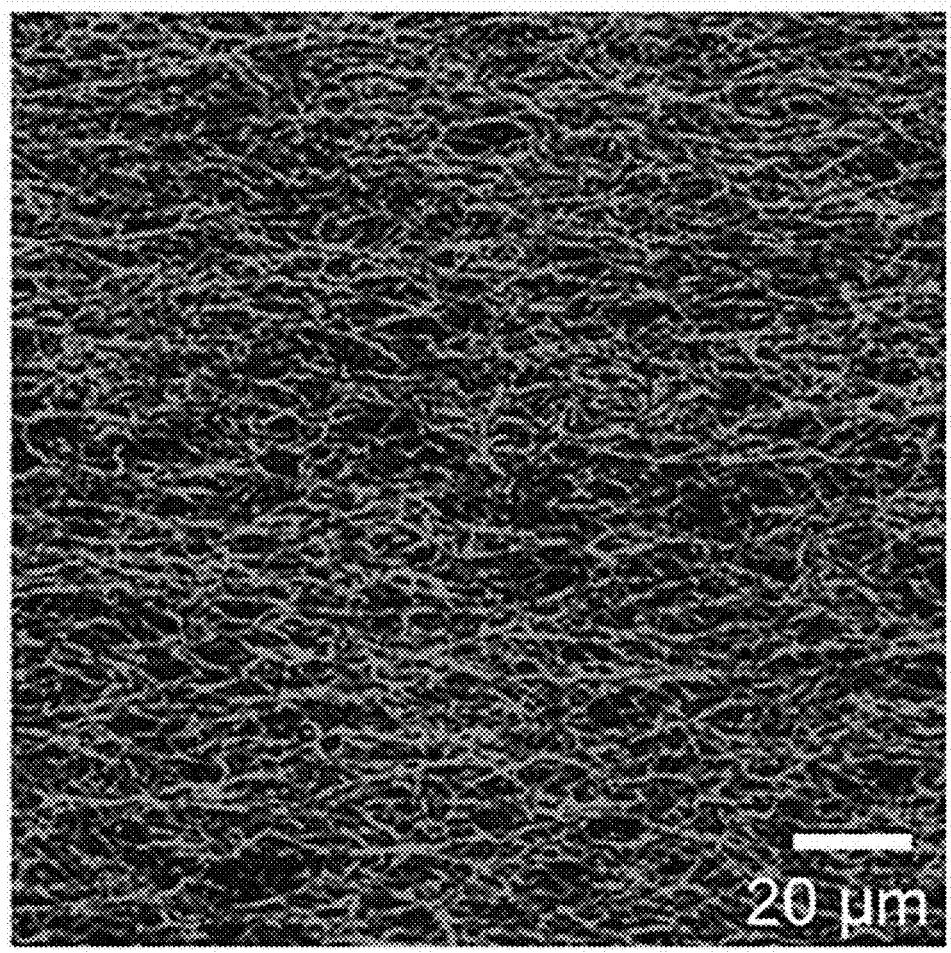
Figure 10D:
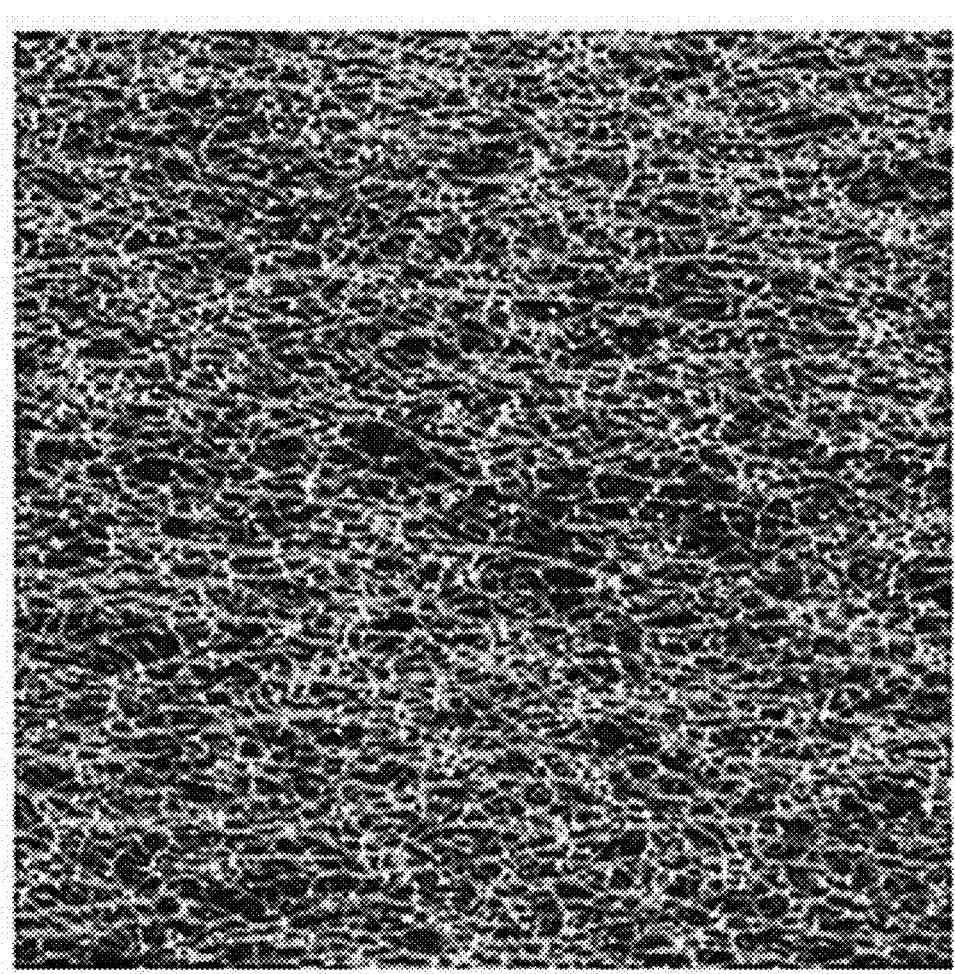
Figure 10E:
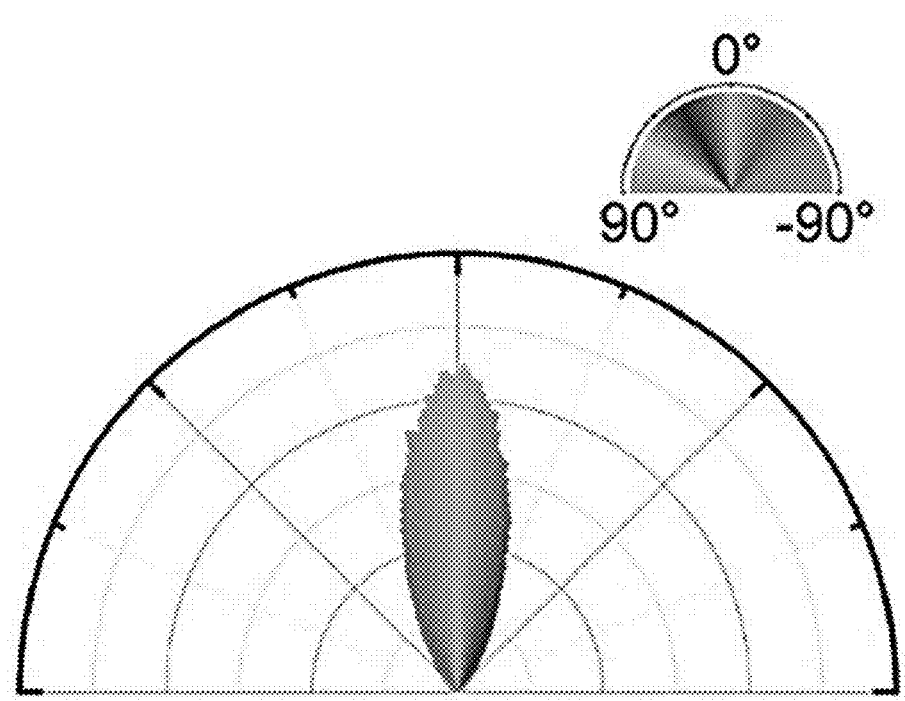

Also, the alignment of the collagen fibers was investigated using the image obtained at 40× magnification (FIG. 10C) as follows. The fiber orientation for each image pixel was analyzed using the OrientationJ plugin of the ImageJ software and color mapping was conducted from −90° to 90° with different colors. The color-mapped image is shown in FIG. 10D. The angle distribution of the color-mapped image was confirmed by drawing a polar plot using the Origin software and the degree of alignment was quantitated by calculating the orientation index (OI). The polar plot is shown in FIG. 10E and the orientation index was calculated using the following equation.

$$OI(\theta_i) = \frac{\sum_{\theta=-90°}^{90°} \cos(2(\theta - \theta_i))N(\theta)}{\sum_{\theta=-90°}^{90°} N(\theta)} \quad [\text{Equation 1}]$$

(where $\theta_i$ is the reference angle with directionality of interest, $\theta$ is the local orientation angle on the image and $N(\theta)$ is the number of pixels corresponding to the local orientation angle)

In this experiment, the reference angle with directionality of interest corresponds to the direction of the restoration axis and it was set to 0° ($\theta_i$=0°). Accordingly, the equation for the orientation index can be simplified as the following Equation 2.

$$OI = \frac{\sum_{\theta=-90°}^{90°} \cos(2\theta)N(\theta)}{\sum_{\theta=-90°}^{90°} N(\theta)} \quad [\text{Equation 2}]$$

For example, if the image is random with no directionality, the OI value is calculated as 0. If the image is oriented along the 0° direction in all the pixels, OI becomes 1. And, if the image is oriented along the 90° or −90° direction in all the pixels, the OI value is calculated as −1. From Equation 2, the orientation index was calculated as 0.74.

From the results of FIG. 10A to FIG. 10E, it was confirmed that, when a channel-coupled scaffold is manufactured by the apparatus or the method according to an aspect of the present disclosure, the collagen fibers contained in the scaffold formed on the channel can be aligned. In addition, it was confirmed from the orientation index value that the collagen fibers are aligned on the PDMS chip along the direction parallel to the compression or restoration direction.

Therefore, in accordance with the apparatus or the method according to an aspect of the present disclosure, when manufacturing the channel-coupled scaffold, the microfibrils such as collagen contained in the scaffold can be aligned along the direction parallel to the compression or restoration direction. Through this effect, when the scaffold contains microfibrils and one or more cell, the cell can also be aligned together.

[Test Example 3] Confirmation of Transport or Diffusion of Material in Channel-Coupled Collagen Scaffold Using Fluorescent Material (1) Preparation of PDMS chip—1) Preparation of PDMS channel layer substrate: The size of a PDMS channel layer substrate was 20 mm (breadth)×20 mm (length)×3 mm (thickness) and the size of three channels located at the center of the substrate was 0.2 mm (width)×0.3 mm (depth)× 15 mm (length). 2) Preparation of PDMS well layer substrate: The size of a PDMS well layer substrate was 20 mm (breadth)×20 mm (length)×7 mm (thickness), the size of a well located at the center was 10 mm (breadth)×5 mm (length)×7 mm (depth), the diameter of inlets and outlets connected to both ends of the channels of the channel layer substrate was 3 mm and reservoirs were provided at the inlets and the outlets for injection of solutions. 3) After treating with oxygen plasma (80 W, 20 sccm, 40 seconds), a PDMS chip was prepared by assembling the PDMS channel layer substrate with the PDMS well layer substrate.

(2) Then, the surface of the assembled chip was coated with polydopamine. Specifically, after adding 2 mg/mL dopamine hydrochloride in 10 mM Tris-HCl buffer (pH 8.5) into the PDMS well and conducting reaction at room temperature for 2 hours, the reaction solution was removed. After washing 3 times with distilled water, the chip was dried in a clean bench.

(3) The PDMS chip was compressed along a direction perpendicular to the channels of the PDMS chip using a compressor as shown in FIG. 8. The compression was performed so that the width of the well along the direction perpendicular to the channel was decreased from its original length of 10 mm to 5 mm.

(4) After loading 20 μL of a fluorescent material (tetramethylrhodamine, TRITC)-labeled collagen solution (25 mg/mL) into the well in the compressed state, the collagen solution was cured partially by maintaining the compressed state at room temperature for 5 minutes.

(5) Then, the PDMS chip was restored from the compressed state. The restored chip was kept in an incubator at 37° C. for 30 minutes for complete gelling of the collagen solution.

(6) A 10 μM FITC dextran (250 kDa) solution (Sigma Aldrich, USA) was introduced as a fluorescent material to the central channel (channel 2 in FIG. 9) through the central inlet and colorless PBS (phosphate buffered saline) was introduced to the channels at both ends (channel 1 and channel 3 in FIG. 9) through the inlets at both ends. After the solutions were introduced to the channels, the levels of the solutions filled in the reservoirs were set equally.

(7) 3-dimensional images were obtained using the LSM700 confocal laser scanning microscope (Carl Zeiss, Germany) at different times (immediately after the injection, 30 minutes after the injection, 1 hour after the injection and 1.5 hours after the injection). Then, the top views and cross-sectional views of the collagen scaffold were obtained through 3D image rendering. The top views are shown in FIG. 11B and the cross-sectional views are shown in FIG. 11C.

Figure 11A:
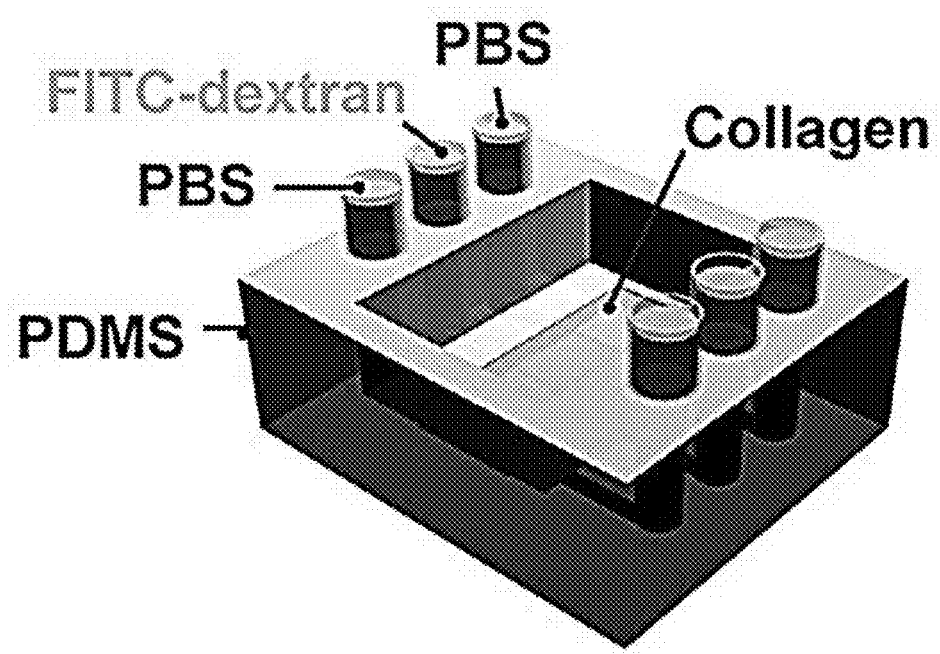
FIG. 11A shows a scaffold including three channels as a channel-coupled scaffold according to an aspect of the present disclosure and FIG. 11B and FIG. 11C show diffusion of a fluorescent material injected into one of the channels.
Figure 11B:
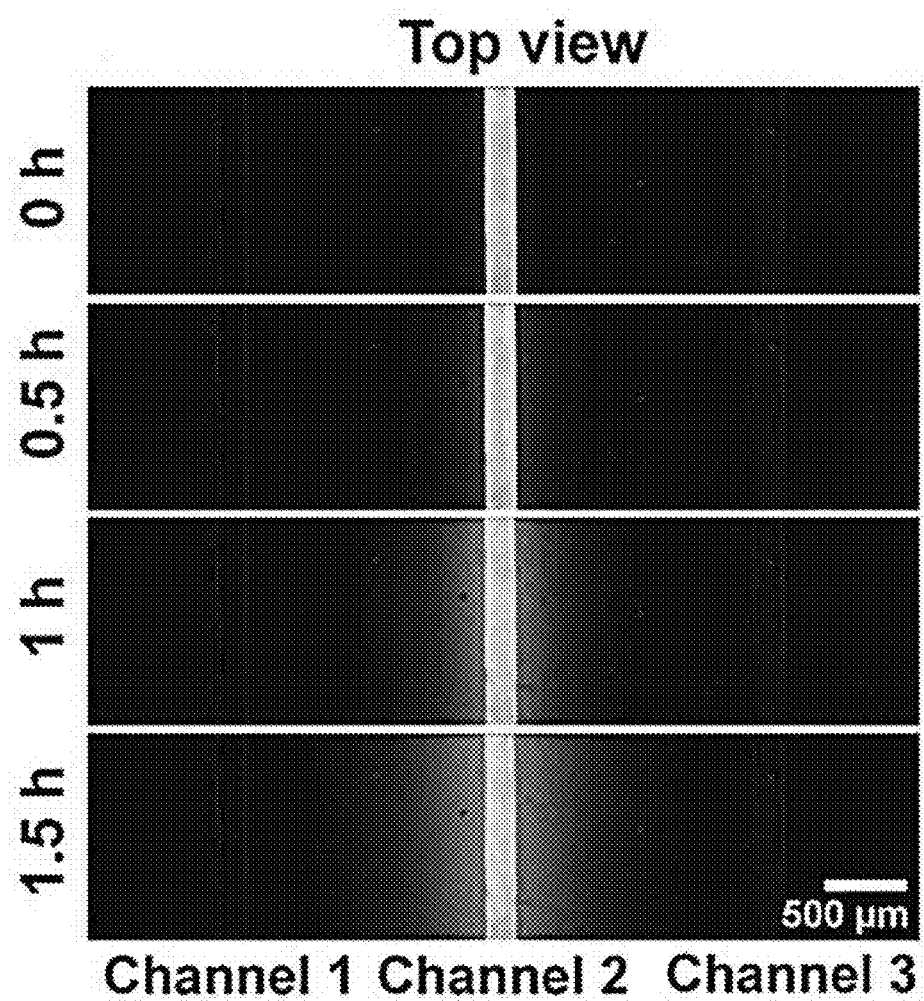
Figure 11C:
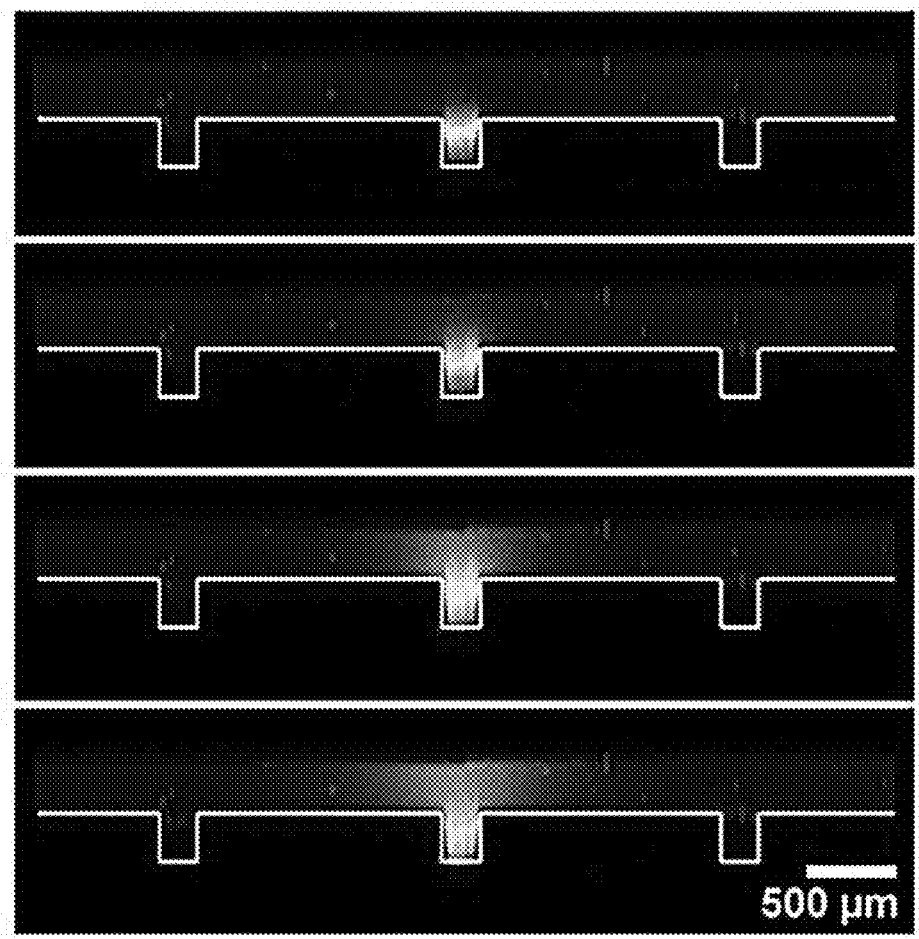

As seen from the top view and cross-sectional view confocal microscopic images of FIG. 11B and FIG. 11C, it was confirmed that a specific material can be transported locally to the collagen gel through the lower channel of the collagen scaffold. Also, it was confirmed that the material introduced to the channel diffuses on the collagen gel with time and a concentration gradient is formed as a result.

[Test Example 4] Confirmation of Transport of Different Materials to Cells Embedded in Channel-Coupled Collagen Scaffold Using Cell-Labeling Fluorescent Materials (1) Preparation of PDMS chip—1) Preparation of PDMS channel layer substrate: The size of a PDMS channel layer substrate was 20 mm (breadth)×20 mm (length)×3 mm (thickness) and the size of three channels located at the center of the substrate was 0.2 mm (width)×0.3 mm (depth)× 15 mm (length). 2) Preparation of PDMS well layer substrate: The size of a PDMS well layer substrate was 20 mm (breadth)×20 mm (length)×7 mm (thickness), the size of a well located at the center was 10 mm (breadth)×5 mm (length)×7 mm (depth) and the diameter of inlets and outlets connected to both ends of the channels of the channel layer substrate was 3 mm. 3) After treating with oxygen plasma (80 W, 20 sccm, 40 seconds), a PDMS chip was prepared by assembling the PDMS channel layer substrate with the PDMS well layer substrate.

(2) Then, the surface of the assembled chip was coated with polydopamine. Specifically, after adding 2 mg/mL dopamine hydrochloride in 10 mM Tris-HCl buffer (pH 8.5) into the PDMS well and conducting reaction at room temperature for 2 hours, the reaction solution was removed. After washing 3 times with distilled water, the chip was dried in a clean bench.

(3) The PDMS chip was compressed along a direction perpendicular to the channels of the PDMS chip using a compressor. The compression was performed so that the width of the well along the direction perpendicular to the channel was decreased from its original length of 10 mm to 5 mm.

(4) After loading 20 μL of a mixture of collagen (25 mg/mL) and a glioblastoma cell line (U87-MG, $10^7$/mL; acquired from Korean Cell Line Bank) into the well in the compressed state, the collagen solution was cured partially by maintaining the compressed state at room temperature for 5 minutes.

(5) Then, the PDMS chip was restored from the compressed state. The restored chip was kept in an incubator at 37° C. for 30 minutes for complete gelling of the collagen solution.

(6) After adding 200 μL of a cell culture medium (MEM (minimum essential medium, Gibco, USA) supplemented with 10% FBS (Corning, USA) and 100 unit penicillin/100 μg/mL streptomycin (Gibco, USA) onto the collagen in the PDMS well and then injecting the cell culture medium to all the channels, incubation was conducted in an incubator at 37° C. under the condition of 5% $CO_2$.

(7) After taking the chip out of the incubator, tubings were connected to the inlets and the outlets in a clean bench. A syringe containing a red cell-labeling fluorescent material (CellTracker™ Red CMTPX) was connected to the tubing connected to the central inlet and syringes containing a green cell-labeling fluorescent material (CellTracker™ Green CMFDA) were connected to the inlets at both ends.

(8) Then, after putting the PDMS chip again in an incubator, the respective solutions were injected at a rate of 5 μL/min for 20 minutes using syringe pumps equipped at the syringes connected to the tubings.

(9) After the injection was completed, the tubings and syringes were removed and 3-dimensional images were obtained using the LSM700 confocal laser scanning microscope (Carl Zeiss, Germany). The result is shown in FIG. 12B.

Figure 12A:
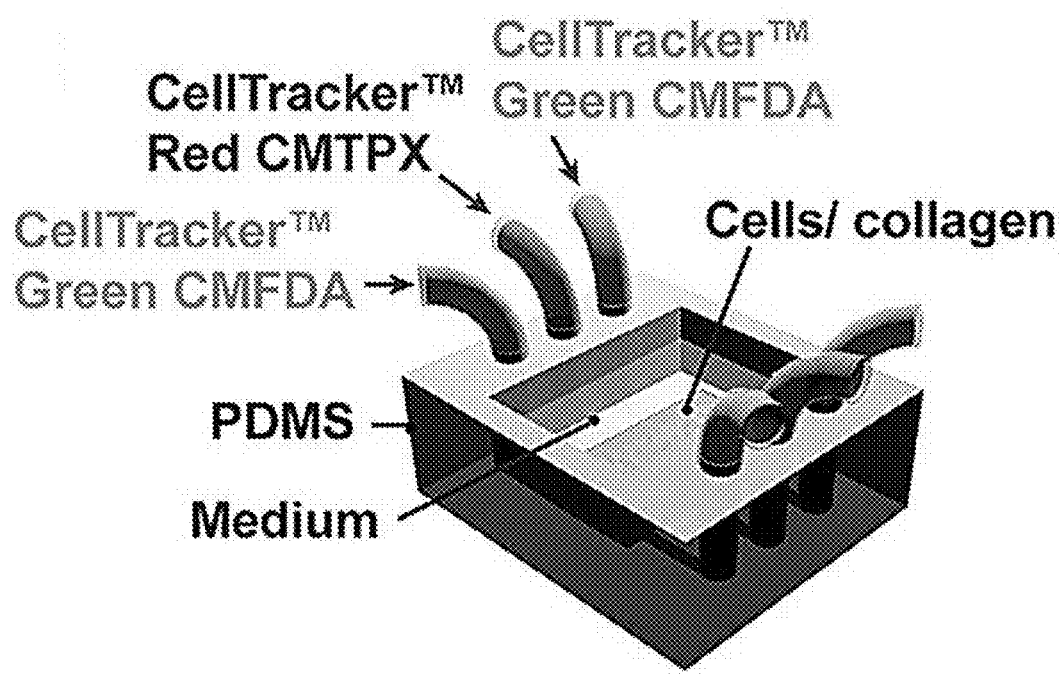
FIG. 12A shows a scaffold including three channels as a channel-coupled scaffold according to an aspect of the present disclosure and FIG. 12B diffusion of different fluorescent materials injected into the channels.
Figure 12B:
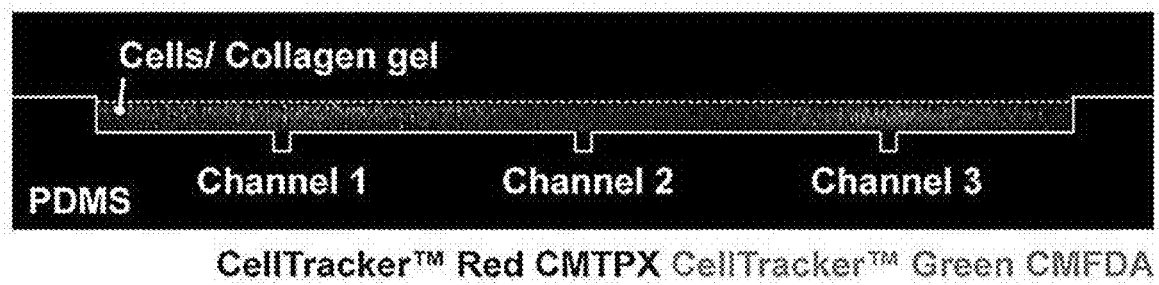

As seen from the cross-sectional view and confocal microscopic 3-dimensional images in FIG. 12B, it was confirmed that the cells embedded at the center portion of the collagen scaffold were stained red by the CellTracker™ Red CMTPX transported through the central lower channel and the cells embedded at both ends of the scaffold were stained green by the CellTracker™ Green CMFDA transported through the lower channels at both ends. That is to say, it was confirmed that different materials can be transported locally to the cells embedded in collagen using the channel-coupled collagen scaffold according to an aspect of the present disclosure.

DETAILED DESCRIPTION OF ELEMENTS

1: second elastic substrate
2: well included in elastic substrate into which scaffold composition is loaded
3: inlet
4: outlet
5: first elastic substrate
6: groove included on surface of first elastic substrate
7: assembly of first elastic substrate and second elastic substrate; elastic substrate chip
8: scaffold composition
9: tubing
10: compression module
11: compression plate
12: compressor
13: controller

What is claimed is:

1. A method for manufacturing a channel-coupled scaffold using an elastic substrate having a facing surface that includes a groove and a non-groove portion, with the groove having an interior defined by at least two edges separated from each other in the facing surface corresponding to the groove being in an open state, the method comprising:
    applying a compressing force to a surface of the elastic substrate, the application of the compressing force forcing the elastic substrate into a compressed state that has the at least two edges, due to the applied compressing force, being in mutual contact so the groove is in a closed state;
    loading a scaffold composition onto the facing surface of the elastic substrate in the compressed state, and into contact with the non-groove portion and the groove that has the at least two edges being in the mutual contact; and
    maintaining the compressed state of the elastic substrate onto which the scaffold composition has been loaded, wherein the loaded scaffold composition is cured partially during the maintaining the compressed state of the elastic substance; and then
    ceasing the application of the force to the elastic substrate, resulting in the at least two edges not being in mutual contact and the groove thereby being in the open state; and
    forming the loaded scaffold composition into a polymer scaffold, the formed polymer scaffold covering the at least two edges across the groove in the open state;
    wherein, in the loading of the scaffold composition, the scaffold composition is not loaded into the interior of the groove in the closed state, and
    wherein the groove forms a channel adjoining the formed polymer scaffold.

2. The method according to claim 1, further comprising coating the facing surface of the elastic substrate with an adhesive prior to the applying of the compressing force.

3. The method according to claim 2, wherein the adhesive is one or more selected from a group consisting of glutaraldehyde, polyethyleneimine, poly-L-lysine, poly-D-lysine and polydopamine.

4. The method according to claim 1, wherein the maintaining of the compressed state includes maintaining the compressed state of the elastic substrate for 1-30 minutes.

5. The method according to claim 1, wherein the applying of the compressing force further comprises applying the compressing force in a direction perpendicular to the length of the groove.

6. The method according to claim 1, wherein, by the application of the compressing force, the elastic substrate becomes compressed by 5-80% of its original width before the elastic substrate becomes compressed along a direction perpendicular to the groove.

7. The method according to claim 1, further comprising forming a concentration gradient of diagnostic or therapeutic material in the formed polymer scaffold by transporting the diagnostic or therapeutic material through the channel to contact the formed polymer scaffold.

* * * * *